United States Patent
Inamdar et al.

(10) Patent No.: US 12,137,512 B2
(45) Date of Patent: Nov. 5, 2024

(54) METHODS AND SYSTEMS FOR MONITORING EVENTS RELATED TO X-RAY TUBES

(71) Applicant: GE PRECISION HEALTHCARE LLC, Wauwatosa, WI (US)

(72) Inventors: Munish Vishwas Inamdar, Bangalore (IN); Kiran Panchal, Bangalore (IN); Rui Xu, Rexford, NY (US); Uwe Wiedmann, Clifton Park, NY (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 808 days.

(21) Appl. No.: 17/165,388

(22) Filed: Feb. 2, 2021

(65) Prior Publication Data
US 2022/0245482 A1    Aug. 4, 2022

(51) Int. Cl.
| | |
|---|---|
| *G06F 17/18* | (2006.01) |
| *A61B 6/58* | (2024.01) |
| *G16H 40/40* | (2018.01) |
| *G16H 40/63* | (2018.01) |
| *H05G 1/54* | (2006.01) |
| *A61B 6/03* | (2006.01) |
| *G01N 23/046* | (2018.01) |

(52) U.S. Cl.
CPC .............. *H05G 1/54* (2013.01); *A61B 6/586* (2013.01); *G16H 40/40* (2018.01); *G16H 40/63* (2018.01); *A61B 6/032* (2013.01); *G01N 23/046* (2013.01)

(58) Field of Classification Search
CPC .......... H05G 1/54; G16H 40/40; G16H 40/63; G01N 23/046; A61B 6/586; A61B 6/032
See application file for complete search history.

(56) References Cited

U.S. PATENT DOCUMENTS

| | | | | |
|---|---|---|---|---|
| 7,748,901 B2* | 7/2010 | Markoff | ............. | G01R 27/2605 378/207 |
| 10,753,969 B2* | 8/2020 | Xu | ........................... | H05G 1/54 |
| 10,930,028 B2* | 2/2021 | Chen | ..................... | A61B 6/544 |
| 11,263,481 B1* | 3/2022 | Takeuchi | ............. | A61B 6/5217 |
| 2018/0315579 A1 | 11/2018 | Yonezawa | | |

FOREIGN PATENT DOCUMENTS

| | | |
|---|---|---|
| JP | 1996078185 A | 3/1996 |
| JP | H0878185 A | 3/1996 |
| JP | 2015092439 A | 5/2015 |

* cited by examiner

*Primary Examiner* — Elias Desta

(57) ABSTRACT

The present approach relates to generating one or both of a failure prediction indication for an X-ray tube or a remaining useful life estimate for the X-ray tube. In one implementation, a complexity of a regression model is selected based on the operating points utilized by an imaging system for the X-ray tube, where the regression model estimates coefficients utilized by a static tube model in estimating health (e.g., thickness) of the electron emitter of the X-ray tube, which in turn may be used in predicting remaining useful life of an electron emitter of the X-ray tube. In another implementation, replacement of an X-ray tube or a component of a filament drive circuit coupled to the X-ray tube may be detected.

6 Claims, 18 Drawing Sheets

METHODS AND SYSTEMS FOR MONITORING EVENTS RELATED TO X-RAY TUBES

BACKGROUND

The subject matter disclosed herein relates to X-ray tubes and, in particular, to monitoring events related to X-ray tubes.

Non-invasive imaging technologies allow images of the internal structures or features of a subject (patient, manufactured good, baggage, package, or passenger) to be obtained non-invasively. In particular, such non-invasive imaging technologies rely on various physical principles, such as the differential transmission of X-rays through the target volume, to acquire data and to construct images or otherwise represent the internal features of the subject.

In such X-ray based non-invasive imaging contexts, X-ray tubes are typically used to generate the X-rays passed through the subject. Examples of imaging systems employing X-ray tubes include, but are not limited to systems for: radiography, mammography, tomosynthesis, C-arm angiography, fluoroscopy, and computed tomography (CT) systems, as well as others. The X-rays emitted by X-ray tubes in such systems are generated in response to control signals during an examination or imaging sequence.

Typically, the X-ray tube includes a cathode and an anode. An emitter within the cathode may emit a stream of electrons in response to heat resulting from an applied electrical current, and/or an electric field resulting from an applied voltage. The anode may include a target that is impacted by the stream of electrons. The target may, as a result of impact by the electron beam, produce X-ray radiation to be emitted toward an imaged volume.

In practice, such X-ray tubes have a finite useful life. However, even X-ray tubes of the same type and model may vary as to their useful life. However, it may be difficult to estimate or predict the useful life of an X-ray tube. As a result, X-ray tubes may either be proactively changed while useful life remains, or may be used until failure, resulting in unscheduled downtime that is inconvenient for patients and staff.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In one embodiment, a method is provided for constructing an X-ray tube model for utilizing in assessing health of an X-ray tube. The method includes acquiring training data points for a respective X-ray tube after installation of the X-ray tube in an imaging system. The method also includes determining a number of operating points utilized in the imaging system for the respective X-ray tube. The method further includes selecting a regression model from multiple regression models based on the number of operating points, wherein each regression model uses the training data points to derive respective values for multiple coefficients.

In another embodiment, a method is provided for assessing health of an X-ray tube. The method includes acquiring data points for a respective X-ray tube installed in an imaging system. The method also includes processing the data points using a trained X-ray tube model to calculate an estimated variable related to emitter resistance. The method further includes calculating a trending indicator based on the estimated variable related to emitter resistance. The method even further includes monitoring the trending indicator for a sudden change. The method still further includes providing an indication when the sudden change occurs on a specific day.

In an additional embodiment, a method is provided for monitoring for replacement of an X-ray tube or a component of a filament drive circuit coupled to the X-ray tube. The method includes acquiring data points for a respective X-ray tube installed in an imaging system. The method also includes processing the data points using a trained X-ray tube model to calculate an estimated variable related to emitter resistance. The method further includes calculating a trending indicator based on the estimated variable related to emitter resistance. The method even further includes monitoring the trending indicator for a sudden change in one direction. The method still further includes upon detecting the sudden change in the trending indicator, flagging the sudden change in the trending indicator as a replacement event for an X-ray tube or a component of a filament drive circuit coupled to the X-ray tube.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

Figure 1:
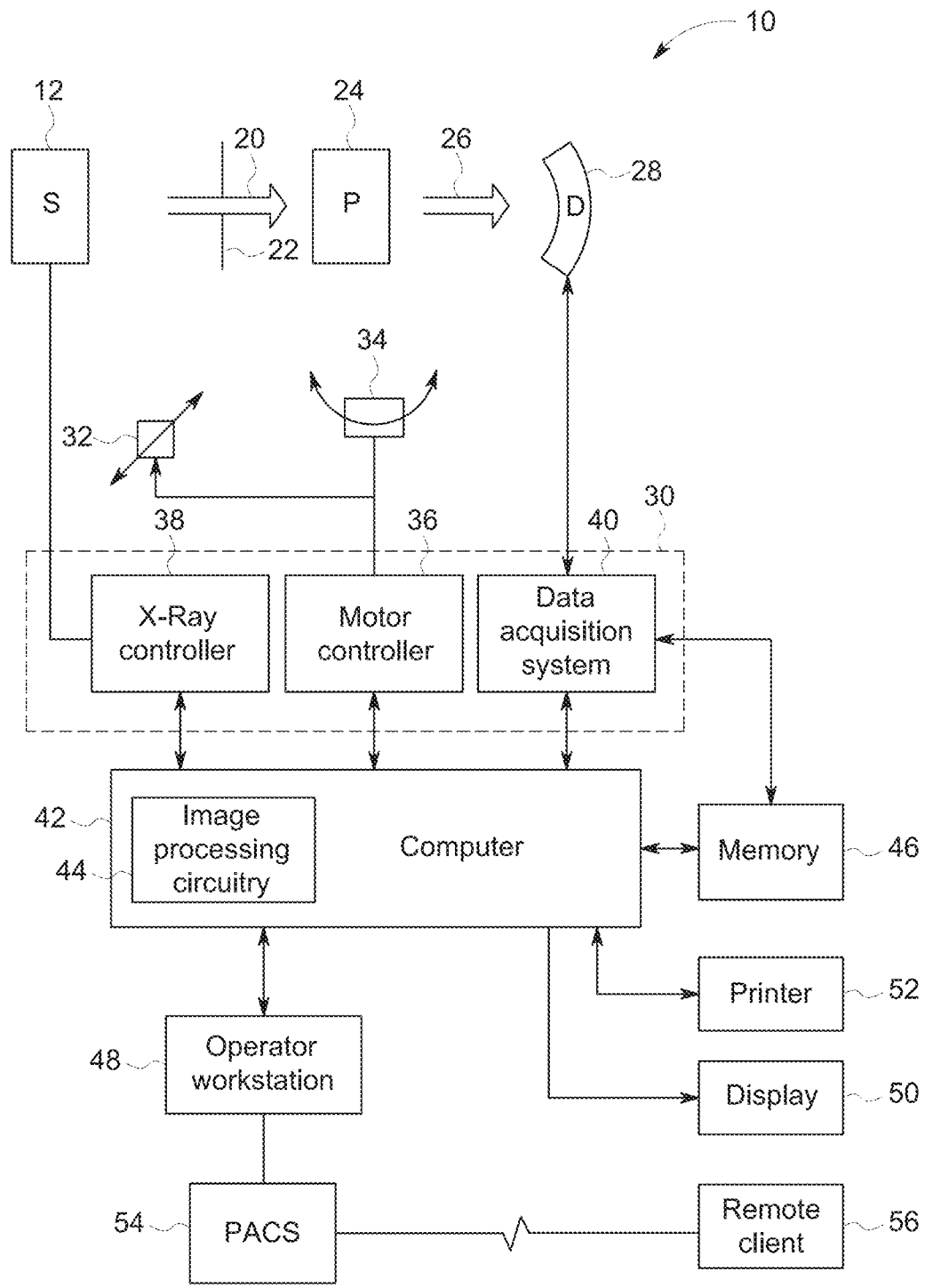
FIG. 1 is a schematic illustration of an embodiment of a computed tomography (CT) system configured to acquire CT images of a patient and process the images in accordance with aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the following discussion is generally provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized with respect to X-ray tubes in other contexts, such as X-ray tubes used in the non-destructive inspection of manufactured parts or goods (i.e., quality control or quality review applications), and/or the non-invasive inspection of packages, boxes, luggage, and so forth (i.e., security or screening applications). In general, the present approach may be desirable in any imaging or screening context in which an X-ray tube is utilized.

As discussed herein, an X-ray tube, such as those used in computed tomography (CT) imaging systems, may be subject to failure for various reasons, including wear-out failures of the rotor (which rotates the anode from which X-rays are emitted) and/or the electron emitter (e.g., a filament) (which emits electrons toward the anode). As used herein, the phrase "X-ray tube failure" may encompass instances in which an emitter of the X-ray tube has failed, even if other emitters are present, due to the loss of capacity of the X-ray tube. Hence, in the present context, the phrase X-ray tube failure may be understood to encompass a failure of an emitter in the X-ray tube, even if the X-ray tube retains some X-ray generation capacity. Such failures may be inconvenient for operators of imaging systems, particularly in instances of unexpected failure of the X-ray tube while the scanner is being used. In accordance with the approach described herein, an algorithm is disclosed that automatically predicts the failure of an X-ray tube with sufficient advance notice to allow a replacement part to be ordered and/or a service call to be scheduled and to allow patient exams to be scheduled appropriately such that disturbances to the examinations are minimized. In an alternative aspect, an algorithm may be provided in addition or instead that provides an estimate of the remaining useful life of the X-ray tube based on the deterioration of the electron emitter (referred to herein as an "emitter" or "electron emitter").

With respect to emitter failures, as the emitter is used it evaporates and is thereby reduced in thickness. As a result, lower emitter currents can achieve the temperatures needed to drive a specified tube current at a specified voltage. By monitoring the evolution of the emitter current needed for a target tube current at any tube voltage, an estimate can be obtained of how far along an emitter is in its life cycle. With this in mind, the present approach is directed to predicting emitter failures before they occur and to estimating the remaining life of the emitter at any stage within the life of the X-ray tube. This present approach is based on modeling the temperature of an emitter, the evaporation rate of the emitter, and the current required to be transmitted through an emitter for a desired tube current and tube voltage setting. In one aspect, the present algorithm can process all combinations of X-ray tube current (mA) and X-ray tube voltage (kV) settings without needing to monitor multiple indicator curves for different current and voltage settings.

In one implementation, a prediction failure algorithm generates an alert only close to the end of the life of the emitter. As a result, an operator would not be actively aware of the health of the emitter until the near the end of the emitter useful life. To provide additional information, in a further embodiment an indicator may be provided that continuously informs the operator about the state of the emitter over time. In one such approach, the respective algorithm may compute a remaining useful life of the emitter at a respective time.

Prior to discussing detailed aspects of the present approach however, an example of an imaging system on which such an approach may be employed is described so as to provide useful context. With this in mind, FIG. 1 illustrates an embodiment of an imaging system 10 for acquiring and imaging data using an X-ray tube in accordance with the approaches discussed herein. In the illustrated embodiment, system 10 is a computed tomography (CT) system designed to acquire X-ray projection data at one or more energy spectra, to reconstruct the projection data into volumetric reconstructions, and to process the image data for display and analysis. The CT imaging system 10 includes one or more X-ray sources 12, such as one or more X-ray tubes.

In certain implementations, the X-ray source 12 may be positioned proximate to a filter assembly or beam shaper 22 that may be used to steer the X-ray beam 20, to define the shape and/or extent of a high-intensity region of the X-ray beam 20, to control or define the energy profile of the X-ray beam 20, and/or to otherwise limit X-ray exposure on those portions of the patient 24 not within a region of interest. In practice, the filter assembly or beam shaper 22 may be incorporated within the gantry between the source 12 and the imaged volume within patient 24.

The X-ray beam 20 passes into a region in which the subject (e.g., a patient 24) or object of interest (e.g., manufactured component, baggage, package, and so forth) is positioned. The subject attenuates at least a portion of the X-rays 20, resulting in attenuated X-rays 26 that impact a detector array 28 formed by a plurality of detector elements (e.g., pixels) as discussed herein. Each detector element produces an electrical signal that represents the energy deposition of incident X-ray photons at the position of the detector element. Electrical signals are acquired and processed to generate one or more projection datasets. In the depicted example, the detector 28 is coupled to the system controller 30, which commands acquisition of the digital signals generated by the detector 28.

A system controller 30 commands operation of the imaging system 10 to execute filtration, examination and/or calibration protocols, and to process the acquired data. With respect to the X-ray source 12, the system controller 30 furnishes power, focal spot location, control signals and so forth, for the X-ray examination sequences. In accordance with certain embodiments, the system controller 30 may control operation of the filter assembly 22, the CT gantry (or other structural support to which the X-ray source 12 and detector 28 are attached), and/or the translation and/or inclination of the patient support over the course of an examination.

In addition, the system controller 30, via a motor controller 36, may control operation of a linear positioning subsystem 32 and/or a rotational subsystem 34 used to move components of the imaging system 10 and/or the subject 24. The system controller 30 may include signal-processing circuitry and associated memory circuitry. In such embodiments, the memory circuitry may store programs, routines, and/or encoded algorithms executed by the system controller 30 to operate the imaging system 10, including the X-ray source 12 and/or filter assembly 22, to process the digital measurements acquired by the detector 28, and/or to monitor and/or estimate X-ray tube emitter health or remaining life in accordance with the steps and processes discussed herein. In one embodiment, the system controller 30 may be implemented as all or part of a processor-based system.

The X-ray source 12 may be controlled by an X-ray controller 38 contained within the system controller 30. The X-ray controller 38 may be configured to provide power, timing signals, and/or focal spot size and locations to the X-ray source 12.

The system controller 30 may include a data acquisition system (DAS) 40. The DAS 40 receives data collected by readout electronics of the detector 28, such as digital signals from the detector 28. The DAS 40 may then convert and/or process the data for subsequent processing by a processor-based system, such as a computer 42. In certain implementations discussed herein, circuitry within the detector 28 may convert analog signals of the photodetector to digital signals prior to transmission to the data acquisition system 40. The computer 42 may include or communicate with one or more non-transitory memory devices 46 that can store data processed by the computer 42, data to be processed by the computer 42, or instructions to be executed by image processing circuitry 44 of the computer 42. For example, a processor of the computer 42 may execute one or more sets of instructions stored on the memory 46, which may be a memory of the computer 42, a memory of the processor, firmware, or a similar instantiation.

The computer 42 may also be adapted to control features enabled by the system controller 30 (i.e., scanning operations and data acquisition), such as in response to commands and scanning parameters provided by an operator via an operator workstation 48. The system 10 may also include a display 50 coupled to the operator workstation 48 that allows the operator to view relevant system data, imaging parameters, raw imaging data, reconstructed data, basis material images, and/or alternative material decomposition images, and so forth. Additionally, the system 10 may include a printer 52 coupled to the operator workstation 48 and configured to print any desired measurement results. The display 50 and the printer 52 may also be connected to the computer 42 directly (as shown in FIG. 1) or via the operator workstation 48. Further, the operator workstation 48 may include or be coupled to a picture archiving and communications system (PACS) 54. PACS 54 may be coupled to a remote system or client 56, radiology department information system (RIS), hospital information system (HIS) or to an internal or external network, so that others at different locations can gain access to the image data.

Figure 2:
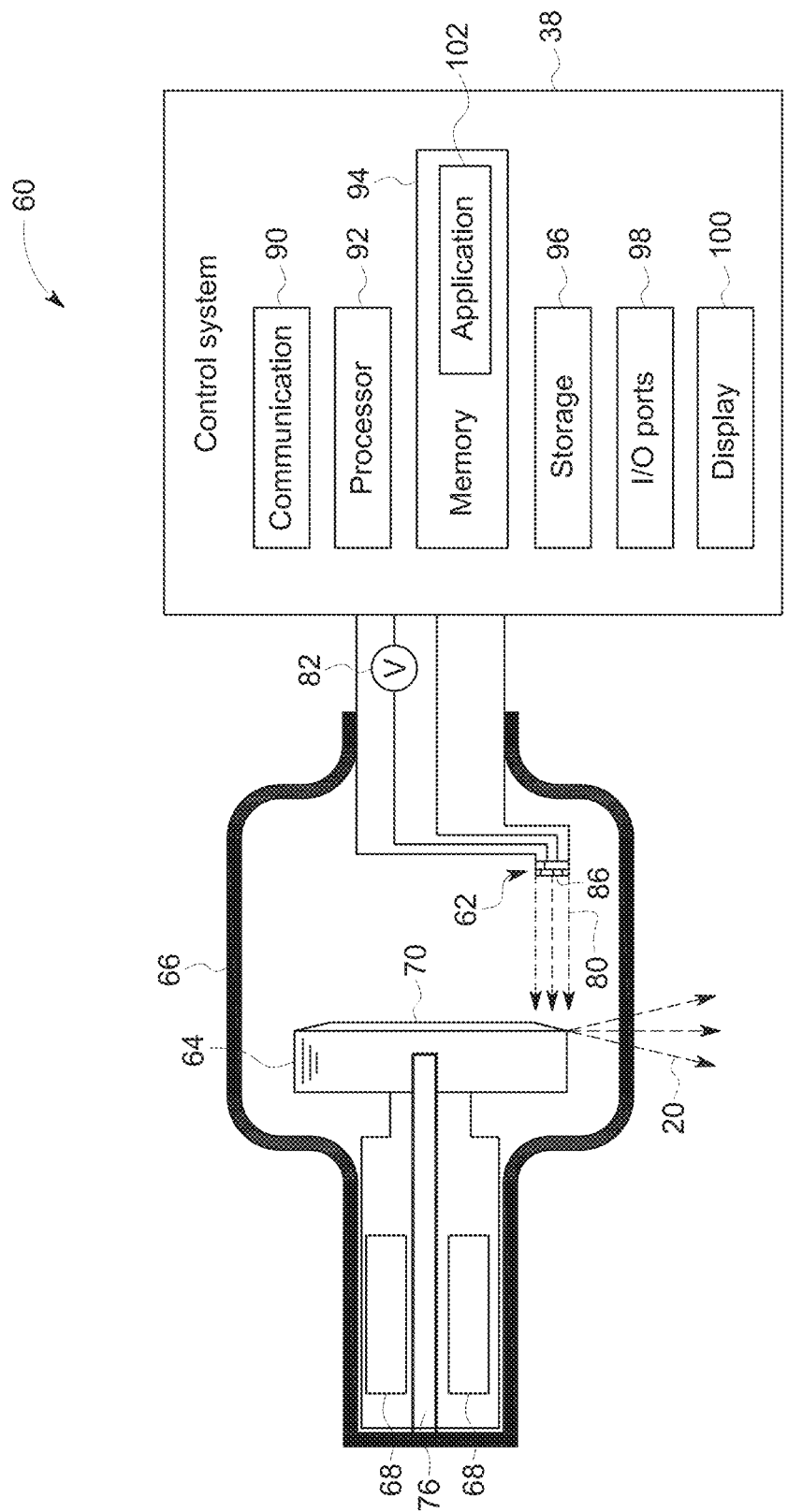
FIG. 2 illustrates a block diagram of an X-ray tube, in accordance with aspects of the present disclosure.

With the preceding discussion of an overall imaging system 10 in mind, FIG. 2 illustrates a block diagram of an X-ray source in the form of X-ray tube 60, similar to an X-ray tube used in computed tomography (CT) machines. As illustrated, the X-ray tube 60 may include a cathode 62 and an anode assembly 64 encased in a housing 66. The anode assembly 64 includes a rotor 68 that may turn an anode 70 (e.g., a rotating anode disc). The anode 70 and the rotor 68 may rotate about a stationary shaft 76.

Figure 3:
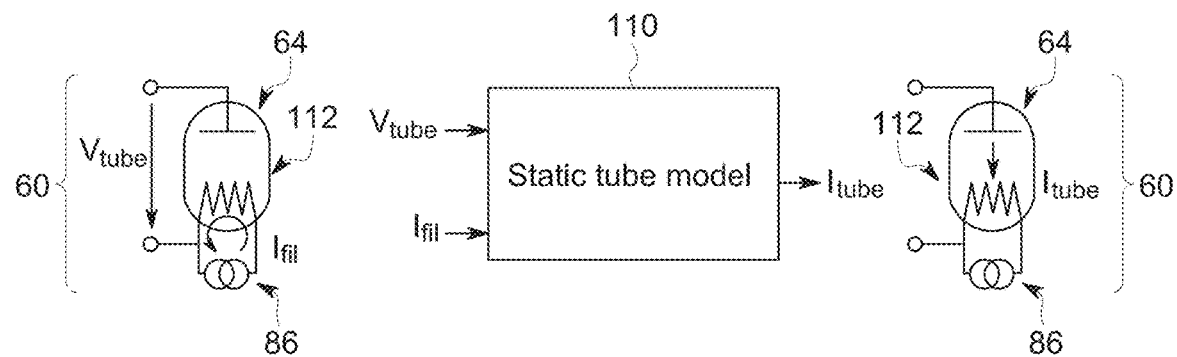
FIG. 3 depicts an example of a static X-ray tube model describing electrical parameters and their interrelationship, in accordance with aspects of the present disclosure.

During operation of the X-ray tube 60, the anode 70 emits an X-ray beam 20 when struck by an electron beam 80 emitted by an electron emitter structure (see FIG. 3, emitter 112) of the cathode 62. In some X-ray tubes, electrostatic potential differences in excess of 20 kV are created between a cathode assembly 86 coupled to voltage source 82 and the anode 70. As such, electrons may be emitted by the cathode assembly 86 that accelerate towards the anode 70, which generates X-rays 20 in response to the incident electron stream.

The X-ray tube 60 is supported by the anode assembly 64 and the cathode assembly 86, with the housing 66 defining an area of relatively low pressure (e.g., a hermetically sealed vacuum enclosure). For example, the housing 66 may include glass, ceramics, stainless steel, or other suitable materials. The anode 70 may be manufactured of any metal or composite, such as tungsten, molybdenum, copper, or any material that contributes to Bremsstrahlung radiation (e.g., deceleration radiation) when bombarded with electrons. The space between the cathode assembly 86 and the anode 70 may be evacuated to minimize electron collisions with other atoms and to increase high voltage stability. Such evacuation may advantageously cause a magnetic flux to interact with (e.g., steer, focus) the electron beam 80.

As noted above with respect to FIG. 1, an X-ray controller 38 of the system controller 30 provides or controls electrical signals to the X-ray tube 60, including to the cathode assembly 86, that provide power, timing signals, and/or focal spot size and locations for the X-ray tube 60 during operation. As such, the X-ray controller 38 has available data related to the electrical parameters used to operate the X-ray tube 60. Such electrical parameters may be maintained over time in an operating log or file that records parameters and electrical conditions for some or all exposure events associated with electron emission by the emitter of the cathode assembly 86. One example of such a log may be a log of exposure information for the system acquired in real time and stored in log files (or otherwise made available) for subsequent retrieval and analysis.

In the depicted example, the X-ray controller 38 (or the overall system controller 30 of which the X-ray controller is one aspect) may include a communication component 90, a processor 92, a memory 94, a storage 96, input/output (I/O) ports 98, a display 100, and the like. Alternatively, some or all of these components may be shared with or may be the comparable components of the computer 42 of the imaging system 10 that additionally handles processing of acquired data and interface with operators and other connected devices. The communication component 90 may be a wireless or wired communication line that may facilitate communication with various other processors, and the like. The processor 92 may be any type of computer processor or microprocessor capable of executing computer-executable code (e.g., computer-executable instructions). The memory 94 and the storage 96 may be any suitable articles of manufacture that can serve as media to store processor-executable code, data, or the like. These articles of manufacture may represent computer-readable media (e.g., any suitable form of memory or storage) that may store the processor-executable code used by the processor 92 to perform the presently disclosed techniques.

The memory 94 or the storage 96 may be used to store data downloaded via the communication component 90. The memory 94 and the storage 96 may be used to store data received via the I/O ports 98, data analyzed by the processor 92, or the like. The memory 94 and the storage 96 may be used to store data providing details regarding operational parameters for the X-ray tube 60, where if the data received via the I/O ports 98 and/or data analyzed by the processor 92 does not satisfy (e.g., exceeds) an operational parameter, the control system 38 may respond by adjusting an operation of the X-ray tube 60 or a system that the X-ray tube 60 is associated with.

The memory 94 or the storage 96 may also be used to store an application 102, a firmware, software, or the like. The application 102, when executed by the processor 92, may also enable the X-ray controller 38 or system controller 30 to assess health of an electron emitter of the X-ray tube 60 as discussed herein. The application 102, when executed by the processor 92, may also enable the X-ray controller 38 or system controller 30 to provide an alert or indication as discussed herein, such as with respect to the degradation of the emitter within the cathode assembly 86. It should be noted that the alert or indication may be provided in any suitable manner (e.g., visual and/or audio alerts) to alert an operator or service personnel to an imminent emitter failure.

With the preceding in mind and to facilitate the subsequent discussion, a number of variables and terms related to the operation of the X-ray tube 60 are provided here. Unless indicated otherwise, the X-ray tube electrical parameters or variables noted below may be obtained or acquired from a log or data store in which exposure data or parameters (e.g., the electoral X-ray tube operating parameters, scan and scanner details, and so forth) are acquired in real time (e.g.., during a scan) and stored for later retrieval and analysis separate from a scan or examination procedure. In particular, as used herein, variables relevant to pre-processing as discussed herein include: a code (i.e., an examination number, from which one can infer exam number, from which one can infer whether an exam is a regular or service exam), time (i.e., a time when generator log data message is sent), an exposure number (Exp_Number) (i.e., an exposure index for an exam), a focus selection (Select_Focus) (i.e., a focus size setpoint (e.g., 1 for small focus and 2 for large focus)), a number of spits per exposure (Num_of_Spits_per_Exp), an examination prescription (Rx_Option) (i.e., a type of CT examination), an average current and/or voltage during an exposure, a current and/or voltage at or proximate to exposure initiation (e.g., at approximately 5 ms), an emitter current and/or voltage during a pre-heat phase, an emitter current and/or voltage at the end of an exposure, a current setpoint (Select_mA), a scan mode (e.g., single or multiple exposure, scan sequence, etc.), and so forth.

With the above parameters and variables in mind, pre-processing of X-ray tube electrical data, as used herein, may include limiting the data employed in assessing emitter life to data points where tube current is greater than a specified minimum, such as 0, tube voltage is within an acceptable range, the CT examination (Rx_Option) and/or scan mode are of a suitable type (e.g., the emitter drive current stays constant for a suitable amount of time, such as for between 0.2 and 5 seconds), the number of spits per exposure is 0, the examination corresponds to the model employed, and the actual X-ray tube current is close to the commanded X-ray tube current, such as within 1%. Data points not meetings these conditions may be discarded from the calculation of the indicator (discussed below) as part of data pre-processing, thus reducing the risk of false positive indications due to corrupt or un-representative measurements. It may be noted, however, that in certain implementations some or all of this data may be retained in the overall exposure count used to determine the slope or other derived parameters, also discussed in greater detail below.

The pre-processed (i.e., cleaned) X-ray tube electrical data points may be provided as inputs to train or use an algorithm for predicting failure or estimate the remaining useful life of an X-ray tube emitter 112, as discussed herein. In one implementation, the present algorithms are based on a static tube model 110 (FIG. 3) that is used to calculate a failure indicator or remaining life estimate based on the residue between the measured and the estimated emitter (e.g., filament) drive current. In particular, given the static tube model shown in FIG. 3, the X-ray tube current $I_{tube}$ can be characterized as a function of emitter (e.g., filament) drive current $I_{fil}$ and the X-ray tube voltage $V_{tube}$. One example of the derivation and parameterization of such a model can be found in U.S. Pat. No. 7,023,960 issued Apr. 4, 2006 to General Electric Company and titled "Method of adjusting the emission rate of radiation from a source of radiation", which is incorporated herein in its entirety for all purposes. Though examples are generally described below in which the estimated emitter drive current is calculated in view of the X-ray tube current, it may be appreciated that it is also contemplated that the estimated X-ray tube current may instead be calculated in view of the emitter drive current and that the estimated X-ray tube current could be used in the same manner as the estimated emitter drive current as described below. Further, an extraction voltage applied to the emitter may also be utilized in the same manner as the estimated emitter drive current as described below. Indeed, the estimation may be of any variable related to emitter resistance. For simplicity only the emitter drive current implementation is discussed in detail below, though one skilled in the art will readily appreciate the applicability of the present discussion to a corresponding use based on an estimated X-ray tube current, extraction voltage applied to the emitter, or any variable related to emitter resistance.

Aspects of the model, such as the model coefficients, can be estimated by fitting a model with the training data, which are usually collected from start life of the X-ray tubes. The predicted emitter (e.g., filament) drive current can then be calculated from the inverse static tube model. Typically, the X-ray tube current at a fixed X-ray tube voltage is a function of the emitter temperature. As the emitter becomes thinner (i.e., evaporates) because of usage, the resistance of the emitter increases and thus the emitter drive current required to attain a target temperature becomes lower. In the case of a round cross-section emitter (e.g., a filament) this approximate proportionality relationship between the emitter current, temperature T and filament diameter d may be characterized by:

$$I_{fil}^2 \propto T^3 d^3 \qquad (1)$$

The proportionality factor depends on the emitter emissivity, which itself depends on the cathode geometry. Additionally, the initial emitter thickness (e.g., filament diameter) may also be subject to variability.

With this in mind, if it is assumed that the temperature is constant, then the quantity $I_{fil}^{2/3}$ must be approximately proportional to the diameter or other measure of thickness. A first order approximation is to assume that for fixed X-ray tube current and X-ray tube voltage settings, the temperature remains constant throughout the life of the emitter. In practice, however, it has been observed that this is not true as the temperature of the emitter does change as the thickness (e.g., diameter) of the emitter decreases, and therefore the proportionality relationship between $I_{fil}^{2/3}$ and the emitter thickness is not accurate. A possible explanation for this might be obtained by noting that hot spots have been observed to develop on the emitter which leads to a non-uniform distribution of temperature on the emitter. Nevertheless, within the context of certain implementations of the present approach, it may be assumed that the general proportionality relation holds with the same constant of proportionality throughout the life of an emitter. To account for variation, it is not assumed that the constant of proportionality remains constant across emitters. Instead, for each emitter, the constant of proportionality is learned from the initial portion of the life of the emitter and it is assumed that this constant remains constant throughout the life of the emitter.

In order to normalize the variation in emitter currents at different kV-mA settings, certain implementations of the present approach normalize to the current observed at the beginning of the life of the X-ray tube at each kV-mA setting. With this normalization, the fractional reduction in the quantity $I_{fil}^{2/3}$ may be used as a proxy to quantify the thinning of the emitter over time. In this manner, the life of a respective emitter at any age t may be represented as:

$$\frac{I_{fil}^{2/3}(t) - I_{fil}^{2/3}(0)}{I_{fil}^{2/3}(0)} \approx \frac{d(t) - d(0)}{d(0)} \qquad (2)$$

where the expression on the left hand side is evaluated at any fixed kV-mA setting. Based on this relationship, the fractional reduction in the emitter current to the power ⅔ is equal to the fractional reduction in the diameter (or more generally thickness) of the emitter. This quantitative assessment of the reduction in emitter thickness may be used as a proxy of indicator of the wear on the respective X-ray tube. In one implementation, this indicator may be denoted as $I^{rel}(t)$ where the superscript denotes that the indicator captures a relative change in the filament current. This may be defined as:

$$I^{rel}(t) := \frac{I_{fil}^{2/3}(t) - I_{fil}^{2/3}(0)}{I_{fil}^{2/3}(0)} \qquad (3)$$

It may be noted that in practice, the quantity $I_{fil}(0)$ is not directly measured but is instead estimated using the emitter model evaluated at the current kV-mA setting. As the emitter model, as discussed herein, is learned using data from the start of life of the X-ray tube emitter, the estimated quantity indeed corresponds to the emitter current that would have resulted on the fresh filament at the operating kV-mA setting.

Figure 4:
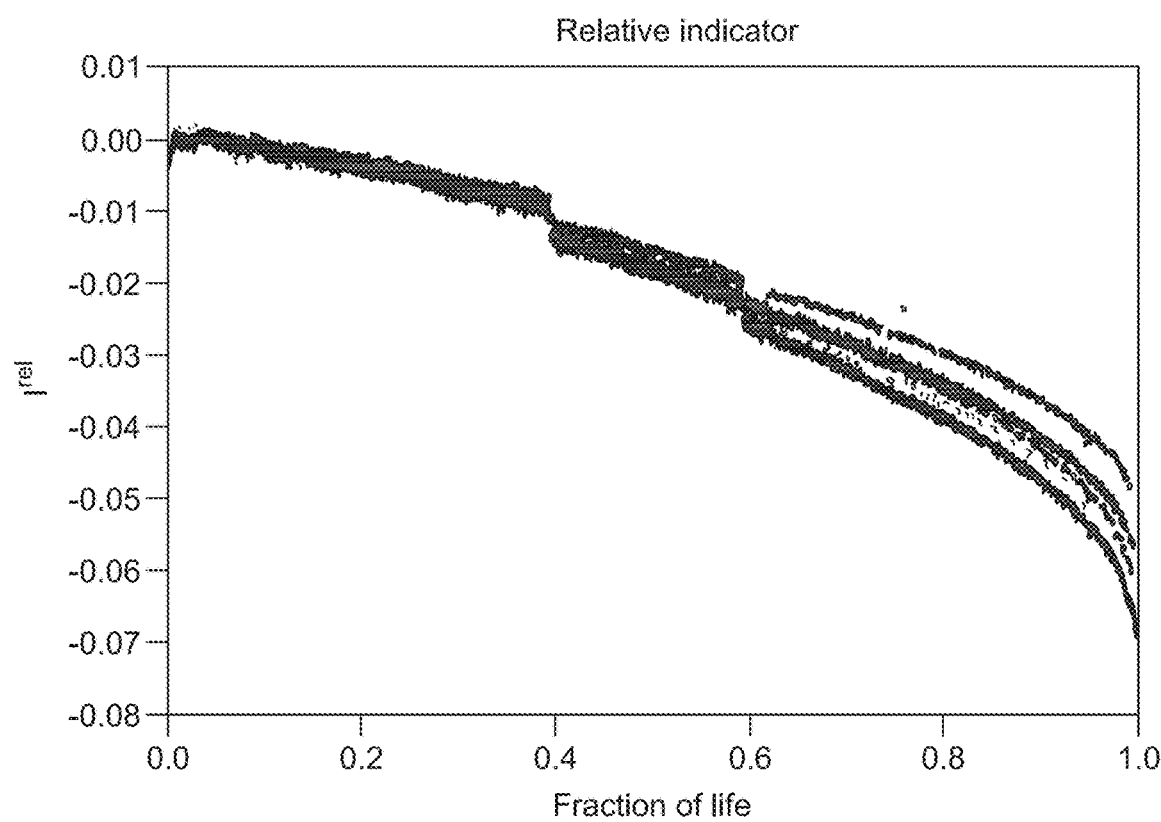
FIG. 4 depicts an example curve plotting an indicator of X-ray tube life, in accordance with aspects of the present disclosure.

With the preceding in mind, in practice, the long-term feedback control system implemented in the X-ray generator automatically adjusts the emitter drive current from one exposure to the next such that the X-ray tube current remains close to the desired setting. Thus, the measured emitter drive currents will be lower than the current predicted using the regression coefficients learned in the initial phase of the emitter. Assuming that constant tube current and tube voltage settings corresponds to a constant temperature, it may be assumed that the relative reduction in the $I_{fil}^{2/3}$ should be proportional to the relative reduction in thickness. As a result, if the indicator $I^{rel}(t)$ of Equation 3 is plotted across the life time of the X-ray tube against a measure of the total usage of the X-ray tube (e.g., the cumulative number of exposures that have been applied using the X-ray tube) a downward-trending curve should be observed. As the emitter approaches failure, the reduction in the emitter current accelerates. As a result, a significant change of this indicator may be observed, in terms of both the magnitude and the slope. An example of this indicator is shown in FIG. 4. In this figure, the fraction of life (x-axis) at any point is measured as the ratio of the total number of exposures that have occurred on the emitter to the total number of exposures on the emitter at failure.

Figure 5:
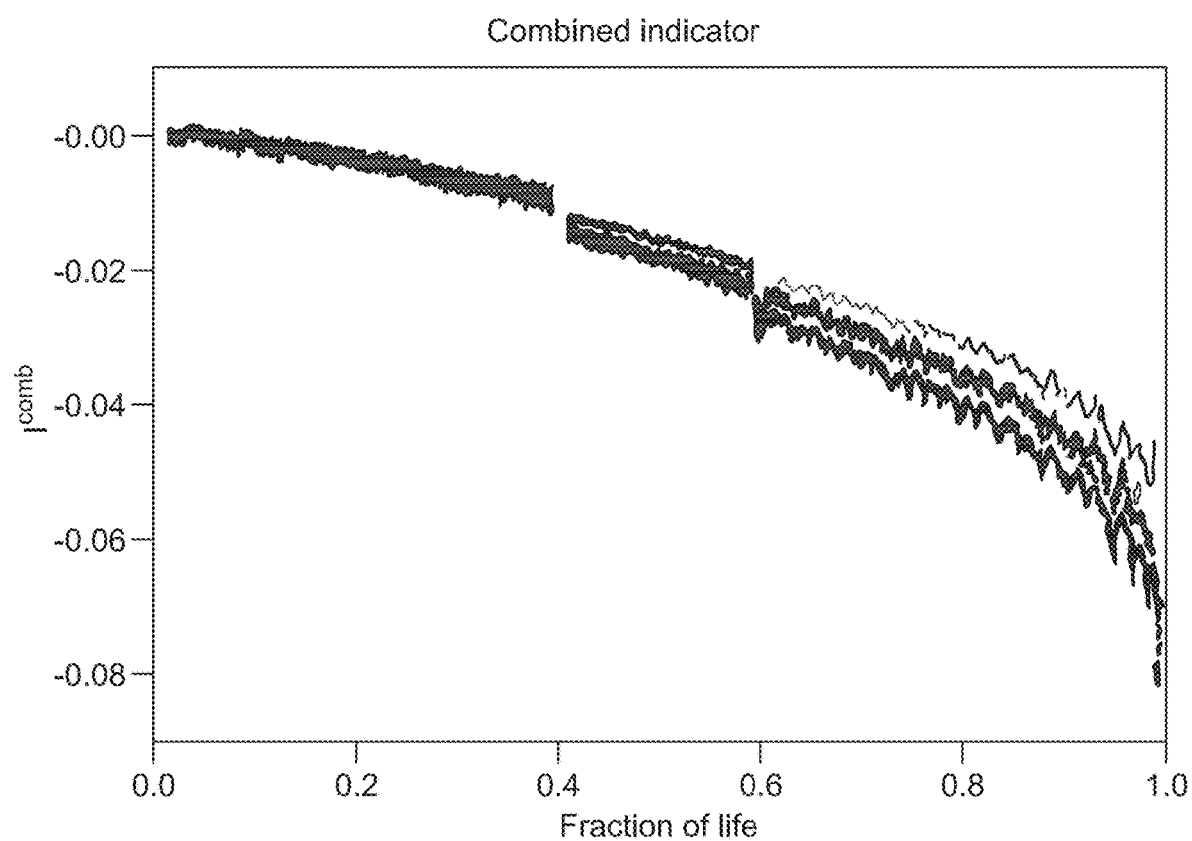
FIG. 5 depicts an example curve plotting a combined indicator of X-ray tube life, in accordance with aspects of the present disclosure.

As seen in FIG. 4, the downward trend in the value of $I^{rel}(t)$ accelerates towards the end of life of the emitter life. Thus, the slope of the indicator provides useful information that can be used to predict emitter failure. In accordance with the present approach, a combined indicator may be employed that combines the value of the indicator with the slope to produce a single indicator:

$$I^{comb}(t) = I^{rel}(t) + 50000|I^{rel}(t)|S^{rel}(t) \qquad (4)$$

where $S^{rel}(t)$ is the slope or the rate of change of $I^{rel}(t)$ relative to the exposure count. The proportionality factor of $|I^{rel}(t)|$ is added to the slope term to emphasize that the slope plays a more significant role in the indicator towards the end of life of the emitter at which point the factor $|I^{rel}(t)|$ will be more significant. In addition, a factor of 50000 is employed in this example based on trial and error to ensure that the final combined indicator does sufficiently utilize the slope information without incurring unnecessary fluctuations. FIG. 5 illustrates the evolution of this indicator as a function of the fraction of life.

Comparing FIGS. 4 and 5, it may be observed that the combined indicator does decrease at a faster rate towards the end of life of the emitter and reaches a lower value at the end. Thus, incorporating the slope information into the indicator helps to improve the detectability of impending failures.

With respect to the generation and use of an emitter failure detection algorithm as used herein, an example of a process and use is provided. This example is provided as a two-step process, with the first step related to modeling the relationship between the emitter drive current and the X-ray tube current and voltage and the second step related to applying the constructed model to monitor incoming data and set alarms for potential failure.

With respect to the first step, an inverse static X-ray tube model ($i_{fil}=f(v,i)$) is built. Usable data is separated into two subsets for small and large emitters, respectively. The following steps are applied separately to each emitter size subset (i.e., applied separately to the large emitter data and to the small emitter data), as the two emitters can be used independently, and therefore they can age at different speeds.

In this example, and with the above constraints in mind, training data points are then collected for linear regression model fitting. In order to ensure the training set has sufficient data points, one approach is to use some threshold time window of data (e.g., the next 1-day, 7-days or 31-days of data) as the training set after the tube installation. If the number of training points is below a threshold (e.g., 1,000, 2,000, and so forth)), one more day of data is added to the training set until the number of training points is above this threshold. For a new X-ray tube, one week of data may be sufficient to build the model.

The mA-kV settings used in the training set are counted. In one embodiment, during the monitoring phase, described below) the algorithm will not consider a new point for further analysis if its mA-kV setting does not appear in the training set.

The regression model $i=f(v, i_{fil})$ is calculated and used to estimate the coefficients. Using these coefficients, the inverse static tube model is constructed. This model may, as discussed below, be used to estimate the emitter drive current by using the estimated coefficients.

Figure 6:
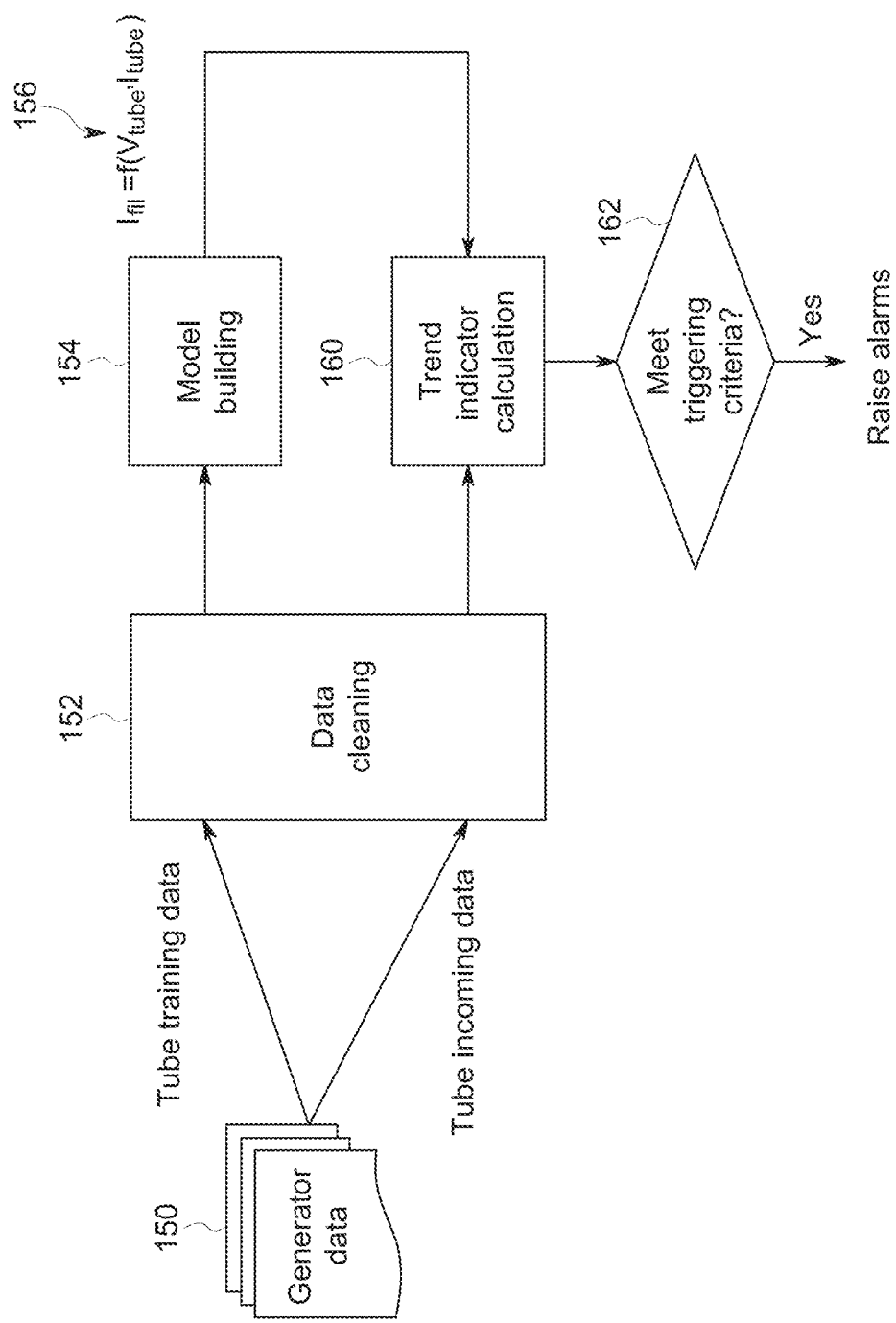
FIG. 6 depicts a flow chart illustrating creation and use of an X-ray tube model used to assess X-ray tube life, in accordance with aspects of the present disclosure.

Turning to FIG. 6, this first step is illustrated with respect to the upper branch of the depicted flow chart. As shown in this example, X-ray tube generator data points 150 are collected over time. In this model training example, some threshold number of points meeting one or more pre-processing criteria (such as those discussed above) are collected for use in training. In the depicted data point pre-processing or "cleaning" occurs at step 152, an output of which are generator data points meeting the established pre-processing criteria and suitable for model building (step 154). As noted above, while data points may be discarded for the purpose of indicator calculation, these points may still be retained as part of the exposure count in the regression used in determining a slope of the curve. Thus, as shown in FIG. 6, model building 154 is performed to generate a model 156 for a respective X-ray tube 60. The model 156 may then be used in monitoring the respective X-ray tube 60 for imminent emitter failure or remaining useful life estimation, as discussed with respect to the second step and as shown in the lower branch of the flow chart of FIG. 6.

With respect to the second step, additional generator data points 150 are collected over time as the X-ray tube 60 is used. Based on new data points 150 and the model 156 (e.g., an inverse static X-ray tube model) the estimated emitter drive current is calculated. In this example, the $i_{fil}$ from the inverse static tube model is the emitter drive current.

The trending indicator, $I^{rel}(t)$, may be calculated as:

$$I^{rel}(t) := \frac{I_{fil}^{2/3}(t)}{(I_{fit}^{est})^{2/3}} - 1 \qquad (5)$$

where $I_{fil}(t)$ denotes the filament current measured in a respective exposure indexed by t.

In one implementation, outliers in the measurements are identified and removed. By way of example, measurements $I^{rel}(t)$ may be used for slope calculation that meet one or more of criteria such as, but not limited to: $I_{rel}(t)<$ Mean(W)+1.0×Std(W), $I^{rel}(t)>$Mean(W)−1.0×Std(W), $I^{rel}(t)<$Mean(W)+2.0×Std(W), $I^{rel}(t)>$Mean(W)−2.0×Std (W), (mA_at_5 ms(t))/(Average_mA(t))<1.1, (mA_at_5 ms(t))/(Average_mA(t))>0.9, (mA_at_exposure_end)/(Average_mA(t))>0.95, (mA_at_exposure_end)/(Average_mA(t))<1.05, (Average_mA(t))/(Commanded_mA)>0.95, (Average_mA(t))/(Commanded mA)<1.05, (mA_at_exposure_end)/(Commanded mA)>0.98, (mA_at_exposure_end)/(Commanded mA)<1.02, and so forth, where W is a window containing the past 1000 points $I^{rel}(t-1000), \ldots, I^{rel}(t-1)$. The purpose of certain of these criteria may be to alleviate the effect of mA unstable, identified as the abnormal behavior for mA_at_5 ms/Average_mA.

For missing data, the time gap between two exposures may be checked to ensure it is above a threshold (e.g., 7 days, 31 days, and so forth). If a gap is detected, the moving window is reset at the first valid data point after the time gap.

In one implementation, the slope $S^{rel}(t)$ of the indicator is calculated using the valid observations in the moving window. The slope is calculated by performing linear regression of $I^{rel}(t)$ against t, which is the raw exposure count prior to outlier removal. In other words, t measures the count of the current measurement in the raw data, and not the count in the data remaining after outlier removal. In one embodiment, data points generated during service exams are also included in the raw exposure count used for slope calculation. Based on the slope $S^{rel}(t)$ of the indicator, the combined indicator, $I^{comb}(t)$, is computed per Equation 4.

Turning back to the flow chart of FIG. 6, this second step is illustrated with respect to the lower branch of the depicted flow chart. As shown in this example, X-ray tube generator data points 150 are collected over time and cleaned, (i.e., pre-processed) as discussed above. The data points, in conjunction with the model 156 are then used to calculate a trend indicator and combined indicator (step 160) as discussed above. If alarm triggering criteria are met (decision block 162) an alarm is generated. If not data collection and processing continues over time.

Although the combined indicator of Equation 4 is a good indicator for predicting emitter failure, the value of the combined indicator is essentially a fractional change in the emitter life which does not have a straightforward practical interpretation. To address this concern, a linearized version of this indicator may be employed that directly measures the fractional remaining life of the emitter.

Figure 7:
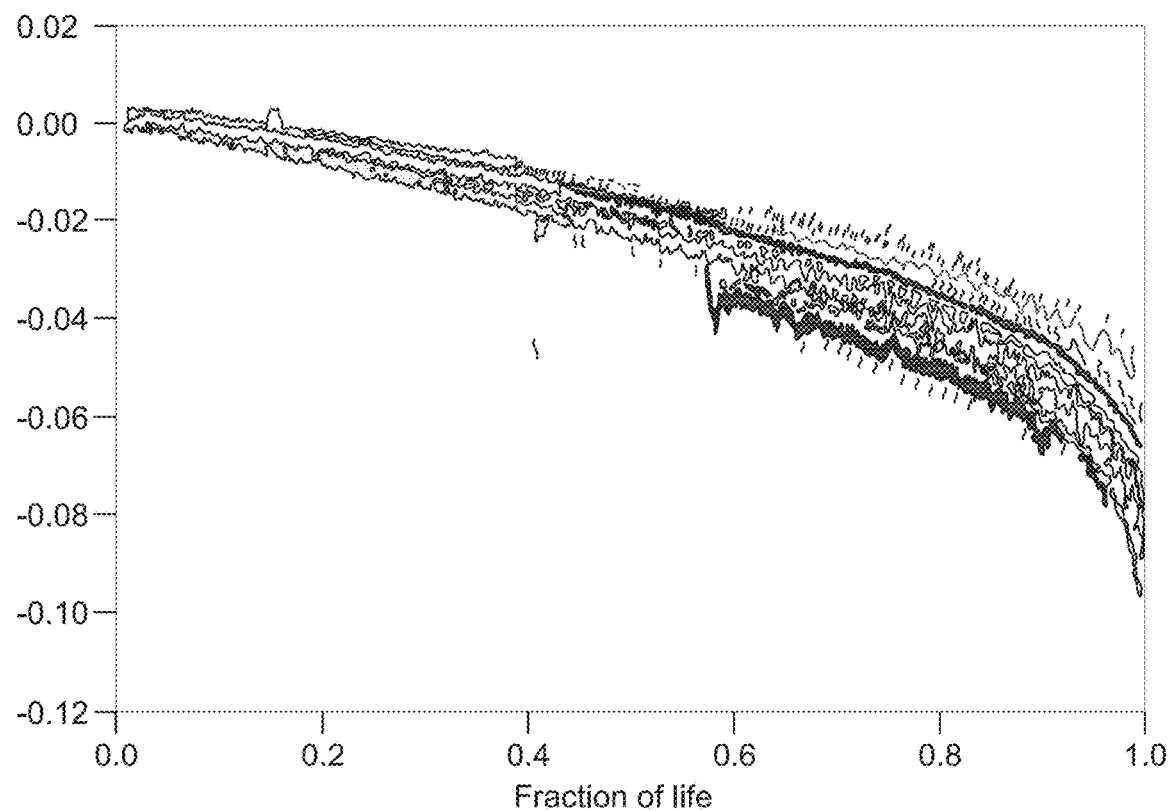
FIG. 7 depicts an example curve plotting combined indicators for a variety of X-ray tubes, in accordance with aspects of the present disclosure.
Figure 8:
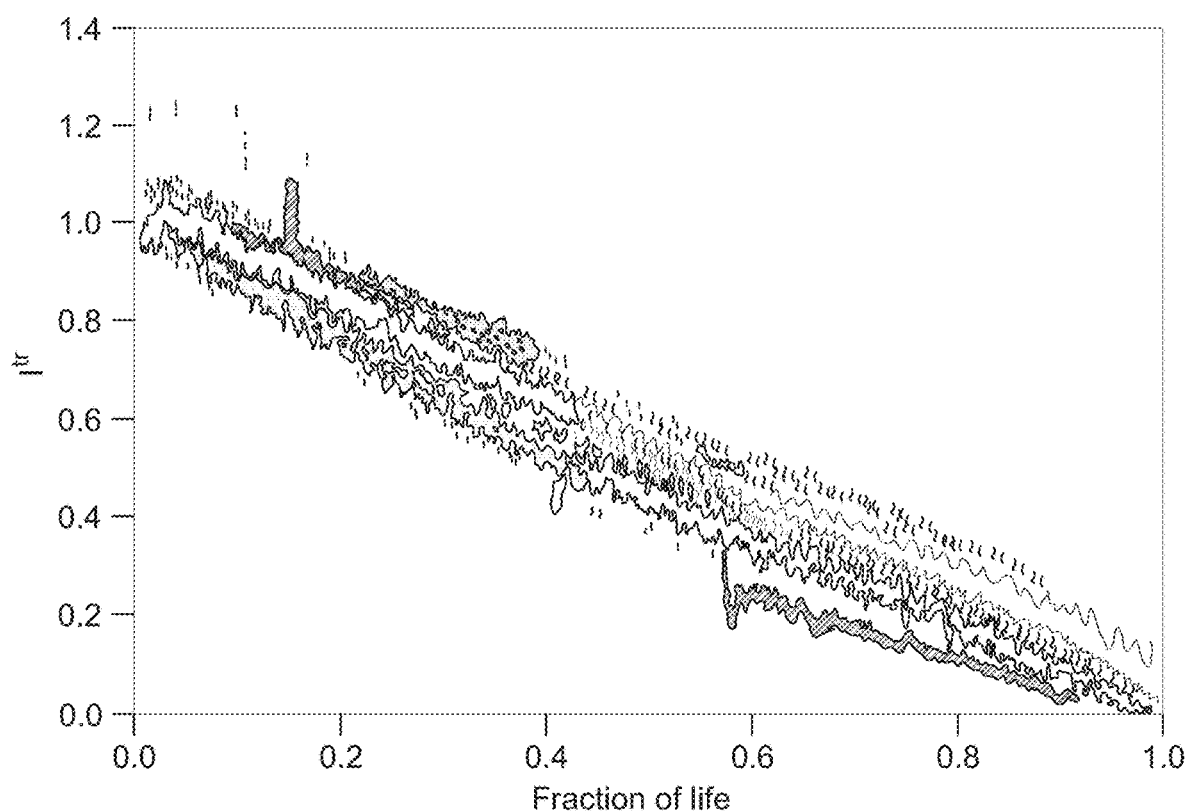
FIG. 8 depicts an example curve plotting linearized version of the combined indicators of FIG. 7, in accordance with aspects of the present disclosure.

By way of example, and turning to FIG. 7, combined indicators for a variety of emitters is depicted. As shown in the figure, each emitter represented tends to follow the same evolution as a function of the fractional life of the emitter. Based on this observation, a model may be fitted to predict the fractional remaining life from the indicator value. This may take the form of a linearized version of the indicator. In one such example, a linearized version of the indicator is obtained by transforming the relative indicator. The transformation may be given by:

$$I^{tr}(I) = \max\{1 - a(1 - e^{bI}), 0\} \quad (6)$$

where a and b are parameters that are learned during the training phase. As seen in FIG. 8, the transformation converts the value of the indicator to a fraction between 0 and 1. The result of the transformation is a linear curve as shown in FIG. 8. In practice, the linear transformation may be used directly on the combined indicator or on a smoothed version of this indicator depending on whether the goal is failure prediction or remaining useful life estimation, both of which are discussed in greater detail below.

With respect to estimating remaining useful life of an X-ray tube, the combined indicator of $I^{comb}(t)$ of Equation 4 may be subject to significant fluctuations due to inaccuracies in the model, the occurrence of unfamiliar usage patterns, and outliers in the data. Hence a remaining useful life estimate that is directly based on this indicator would be correspondingly noisy and subject to fluctuation. These concerns may be addressed by smoothing the indicator. Thus, for remaining useful life estimation, the transformation of Equation 6 may be applied to a smoothed version of the combined indicator of $I^{comb}(t)$ given in Equation 4. In other words, the curves associated with a combined indicator, such as those shown in FIG. 7, may be modeled using a model of the form of Equation 6.

In this approach, the algorithm used to learn the model is applied to the combined indicator of Equation 4, and not to the relative indicator of Equation 3. Another difference is in the calculation of the fractional remaining life used in the training phase. Instead, the fractional number of exposures left may be used as the fractional remaining life due to, in almost all sites observed, the usage rate remaining constant over the entire life of the emitter. Hence, the fractional cumulative wear is approximately equal to the fractional number of exposures. In view of this observation, there is little or no gain in choosing a computationally complex quantity, such as the cumulative wear, instead of simply using the exposure count. A further variation in implementation may be employing a weighted fit (in which higher weights are assigned to the errors at the end of life of the emitter) while performing the fit. This ensures that the fit is accurate towards the end of life of the filament, which is the regime of interest for failure prediction.

With the preceding in mind, in one example of an implementation steps such as the following may be performed to learn a model useful to estimating remaining useful life of an X-ray tube.

With respect to learning the model, for each failed emitter, use the available data to compute the combined trending indicator of Equation 4. The combined trend indicator so calculated, a median filter is applied over a window of exposure (e.g., over 300 exposures) to generate a smoothed indicator. The smoothed indicator at any time is the median of the indicators measured during the past window (e.g., 300) of valid exposures that pass the outlier removal test and the missing data test discussed herein. In this example, let S denote the smoothed indicator obtained by computing the median of the past window of exposures (e.g., 300 exposures).

For each data-point the fractional remaining life, denoted R, may be computed in accordance with:

$$R = \frac{\text{Number of exposures at failure} - \text{Number of exposures completed so far}}{\text{Number of exposures at failure}} \quad (7)$$

The fractional remaining life after any exposure may be denoted as R.

A weighted non-linear regression of R against S is performed, assuming a functional form of Equation 6, to obtain a non-linear fit of the form:

$$R \approx \max\{1 - a(1 - e^{bS}), 0\} \quad (8)$$

and the fitted values for parameters a and b are obtained. The weight assigned to the error at each data-point is proportional to $(1-R)^2$ in order to emphasize the fit accuracy at values of R close to 0, or equivalently, at data-points close to the end of life of the filament. In one embodiment, in performing the regression only data-points following the first 5000 exposures are used.

Once the model is learned values of parameters a and b are available. One aspect of this approach is that the model can be continuously updated whenever data from more failed filaments become available. The processed data from these filaments can also be added to the training set to improve the robustness and accuracy of the parameter estimates.

The model, once learned, can be used to predict the remaining useful life of other emitters. The steps involved in predicting the remaining useful life of an emitter, in one example, may include the following. For a current emitter of interest, available data for the respective emitter is used to calculate the combined trending indicator in accordance with Equation 4. The normalized trend indicator so computed is smoothed, such as using a median filter over some window of exposures (e.g., 300 exposures). Thus, the smoothed indicator at any time is the median of the indicators measured during the past window of exposures. The smoothed indicator obtained by computing the median of the past window of exposures may be denoted S.

For each measurement of the smoothed indicator, the time difference is calculated between the earliest and latest samples. This time difference may be used in calculating the median. In certain implementations, a threshold may be imposed such that a time difference exceeding threshold (e.g., 25 calendar days) is deemed too great and no median is calculated over that window due to lack of current or "fresh" data.

The computed value of S and relation shown in Equation 1 are used with the learned values of the parameters a and b to compute the estimate of the remaining fractional life R as:

$$R^{est} = \max\{1 - a(1 - e^{bS}), 0\} \quad (9)$$

In one implementation, the estimated value of R may be reported differently depending on whether the model is undergoing training or is fully trained. For example, in such an implementation, a value of "1" (i.e., full life) may be reported while the model is undergoing training while the calculated value is instead returned when the model is trained.

As may be appreciated with respect to the preceding steps, the output of the above algorithm is the fraction of the remaining life of the emitter. In performing such estimation, an assumption that the usage rate of the emitter will remain substantially fixed or constant is implicit. The output of the above algorithm can be transformed into the remaining life in absolute calendar time with additional information such as the current age of the filament in calendar time.

Although the smoothed combined indicator S described above is useful as a remaining life estimator, it may not be as suitable for impending failure prediction due to smoothing of the indicator tending to average out abrupt transitions in the indicator. In practice, abrupt drops in the value of the combined indicator are common at the end of life of the emitter, which is one of the justifications for incorporating the slope into the combined indicator. Therefore, for failure prediction it may be more useful to rely not on the smoothed indicator, but on a processed version of the raw combined indicator of Equation 4.

With this in mind, a prediction algorithm for predicting emitter failure is summarized below. The described prediction algorithm includes two aspects: modeling the relation between the emitter drive current and X-ray tube current and voltage, and applying the constructed model to monitor incoming data and set alarms for potential failure. Note that, in one implementation, the data used with respect to the prediction algorithm has undergone preprocessing steps as described above.

With respect to the steps, the trending indicator $I^{rel}(t)$ of Equation 5 and the combined indicator $I^{comb}(t)$ of Equation 4 are computed. The unsmoothed combined indicator is transformed to get an unsmoothed remaining fractional useful life estimate in accordance with:

$$R^{rough}(t) = \max\left\{1 - a\left(1 - e^{bI^{comb}(t)}\right), 0\right\} \quad (10)$$

It may be noted that in this example the transform is performed on the unsmoothed combined indicator (rather than the smoothed indicator used for the remaining useful life estimate described above) so that abrupt changes may have an effect, as mentioned above. Alternatively, instead of not applying any smoothing at all, a less aggressive smoothing (e.g. using a lower number of exposures for the window used for median calculation) may be applied.

The number of remaining days of useful life of the respective emitter may be estimated as:

$$D(t) = \frac{N(t)}{1 - R^{rough}(t)} - N(t) \quad (11)$$

where N (t) is the total age of the filament obtained by calculating the difference between the current date stamp and the X-ray tube installation date.

For pending or imminent emitter failure notification, one or more alarm criteria may be established. For example, in one embodiment, an alarm or notification may be generated when the following condition is met:

$$\max\{D(t), D(t-1), D(t-2), D(t-3), D(t-4)\} < Thr \quad (12)$$

where Thr is a configurable threshold that represents the lead time prior to emitter failure for which a notification is desired. In this example implementation, the triggering criteria requires 5 consecutive points that meet the threshold, which helps alleviate the effects of outliers.

It may be noted that, in an implementation where both remaining useful life estimation and failure prediction are performed, the above sequences of steps may be modified to facilitate performing both algorithms. For example, in the implementation of the remaining useful lifetime estimate described above, smoothing of the combined indicator was described as being performed prior to applying the non-linear transform of Equation 6.

However, the smoothing operation is performed using a median filter, and thus there would be no significant difference in the final estimator if the smoothing was instead performed after the non-linear transformation. Therefore, in an alternative implementation, the non-linear transform may be performed first on the unsmoothed combined indicator so that the result of the non-linear transform operation can be used for both the remaining useful life estimate as well as the alarm generation (i.e., failure prediction) aspect. Adopting this sequence of operations would obviate the need to repeat the non-linear transform on the smoothed signal while computing the remaining useful life estimate.

Figure 9:
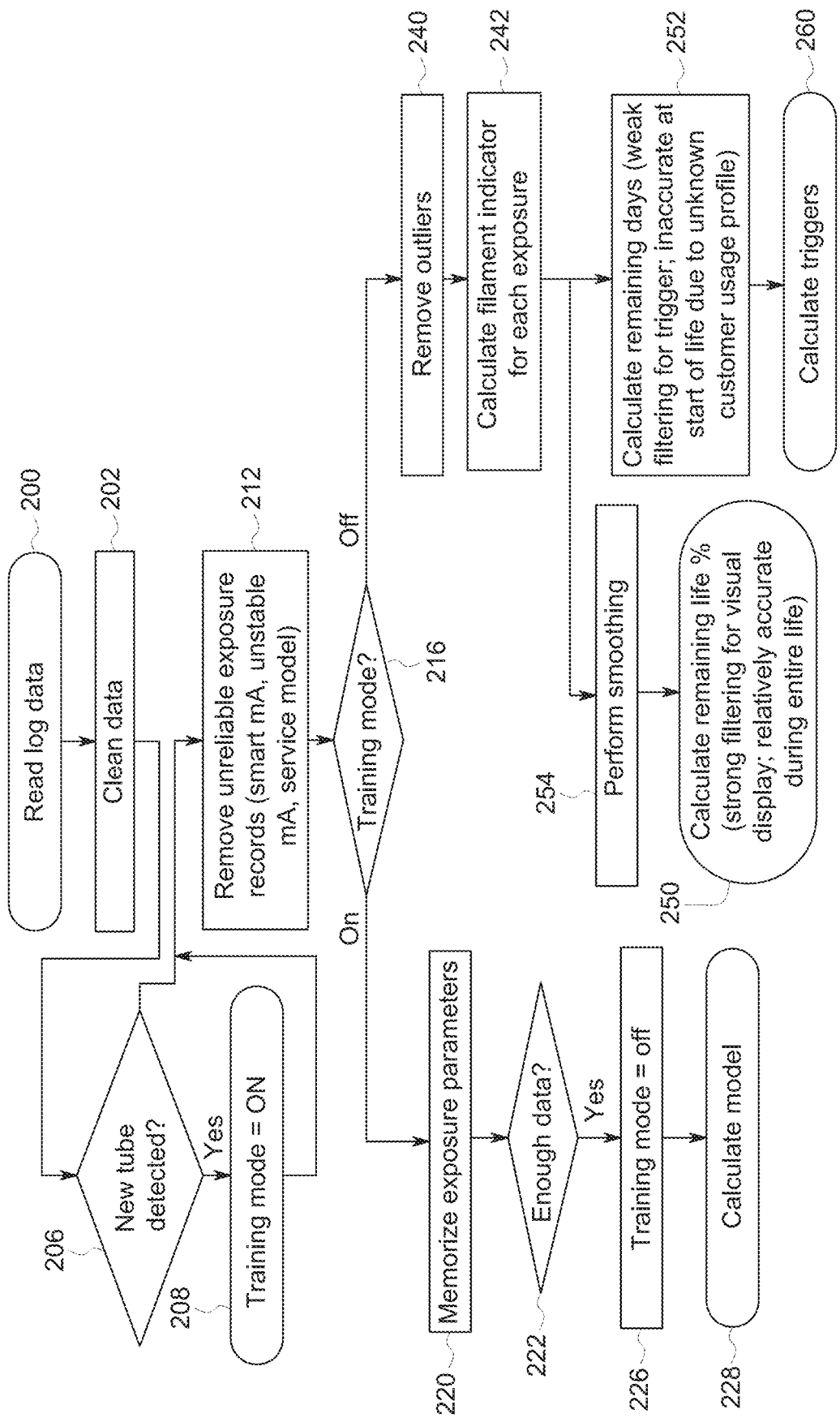
FIG. 9 depicts a flow chart illustrating creation and use of an X-ray tube model used to assess X-ray tube life depicts an example curve plotting an indicator of X-ray tube life, in accordance with aspects of the present disclosure.

An illustration of the proposed pipeline for performing all the steps needed for training the model, for remaining useful life estimation, and for alarm generation is provided in FIG. 9. In this example, data characterizing the electrical operating parameters of each exposure event are acquired, such as at depicted Step 200 at which log data is read from a log file. At Step 202, the acquired log data may be cleaned as discussed herein to remove data points deemed not representative or appropriate for the purposes of modeling or evaluation using a model.

In the depicted example, a determination (decision block 206) is made as to whether the X-ray tube 60 in question is a new X-ray tube. As noted herein, this may be based upon whether data exists for the tube for some threshold number of days (e.g., seven days) or based upon other criteria, such as the presence of a new tube indicator or flag in the respective database, the presence or absence of a model associated with the X-ray tube and so forth. If a new X-ray tube 60 is determined to be present, a training mode of the depicted pipeline is set to ON (Step 208). If the X-ray tube 60 is not new, a trained model exists and new data points will be processed by the existing model for remaining life estimation and/or emitter failure prediction.

In the depicted implementation, once the new tube detection determination is made the acquired data points may be processed to remove data points associated with unreliable exposure events (Step 212), unstable mA, and so forth). Based on whether the model training mode is set to ON or OFF (decision block 216) one of two paths may be followed. In the event the model training mode is set to ON, exposure parameters based on the data points are stored or memorized (Step 220) until a threshold amount of data is acquired (decision block 222). Once the threshold amount of data is available, the training mode is set to OFF (Step 226), and the model calculated (Step 228) as discussed herein.

Returning to Step 216, when the model training mode is set to OFF, the acquired data points are processed to remove outliers (Step 240), such as based upon an absolute or statistical threshold. An emitter (e.g., filament) indicator is calculated (Step 242) for each exposure event. The indicator may then be used in one or both of calculating a remaining life percentage of the emitter (Step 250) or calculating a remaining number of days (Step 252) of the emitter. In the context of calculating a remaining life percentage of the emitter, as discussed above, a smoothing Step 254 may be performed before performing the calculation. In the context of calculating a remaining number of days (Step 252) of the emitter, the calculated number of days may be used to calculate (Step 260) whether one or more trigger conditions are met for generating a notification or alarm of pending emitter failure within a configured time frame.

Figure 10:
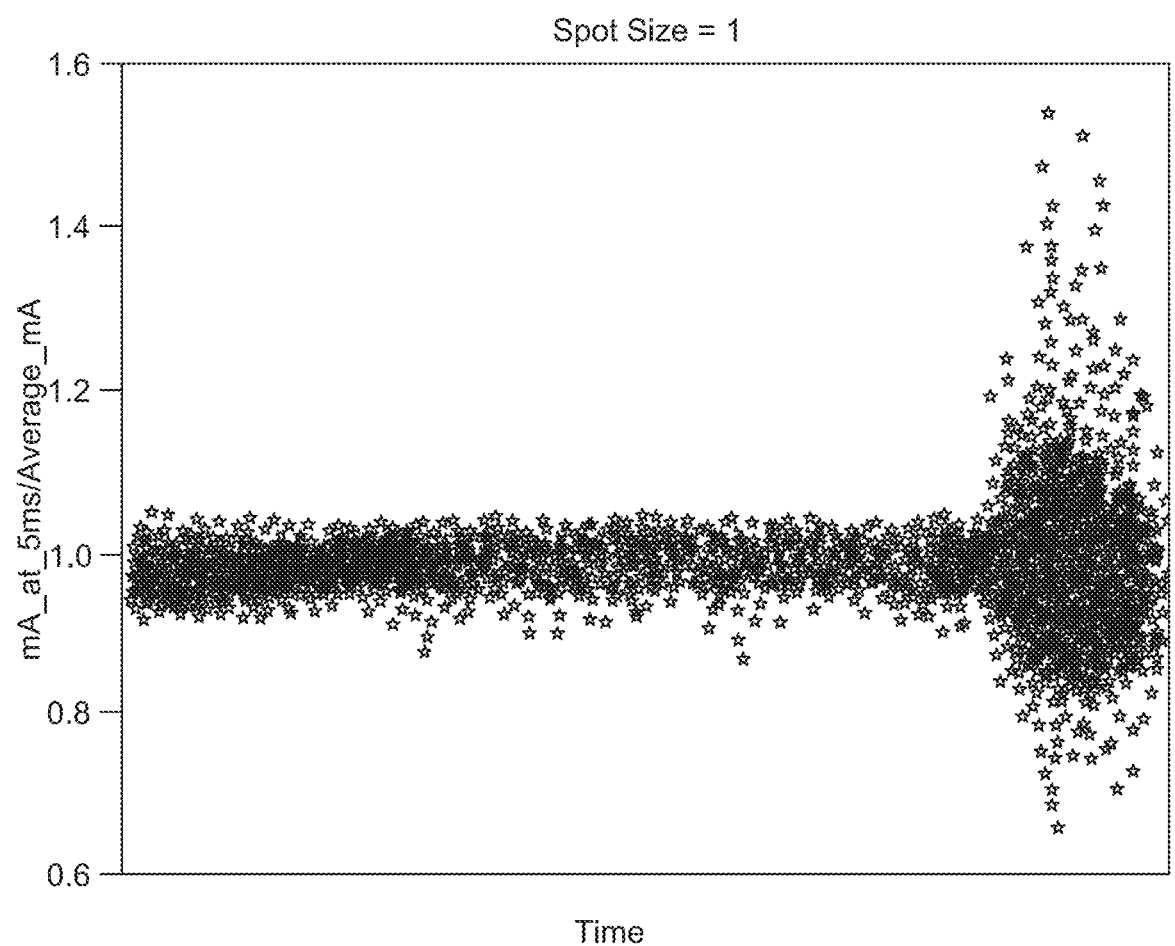
FIG. 10 depicts a plot of mA at 5 ms/average mA over a window of time exhibiting an unstable mA behavior.
Figure 11:
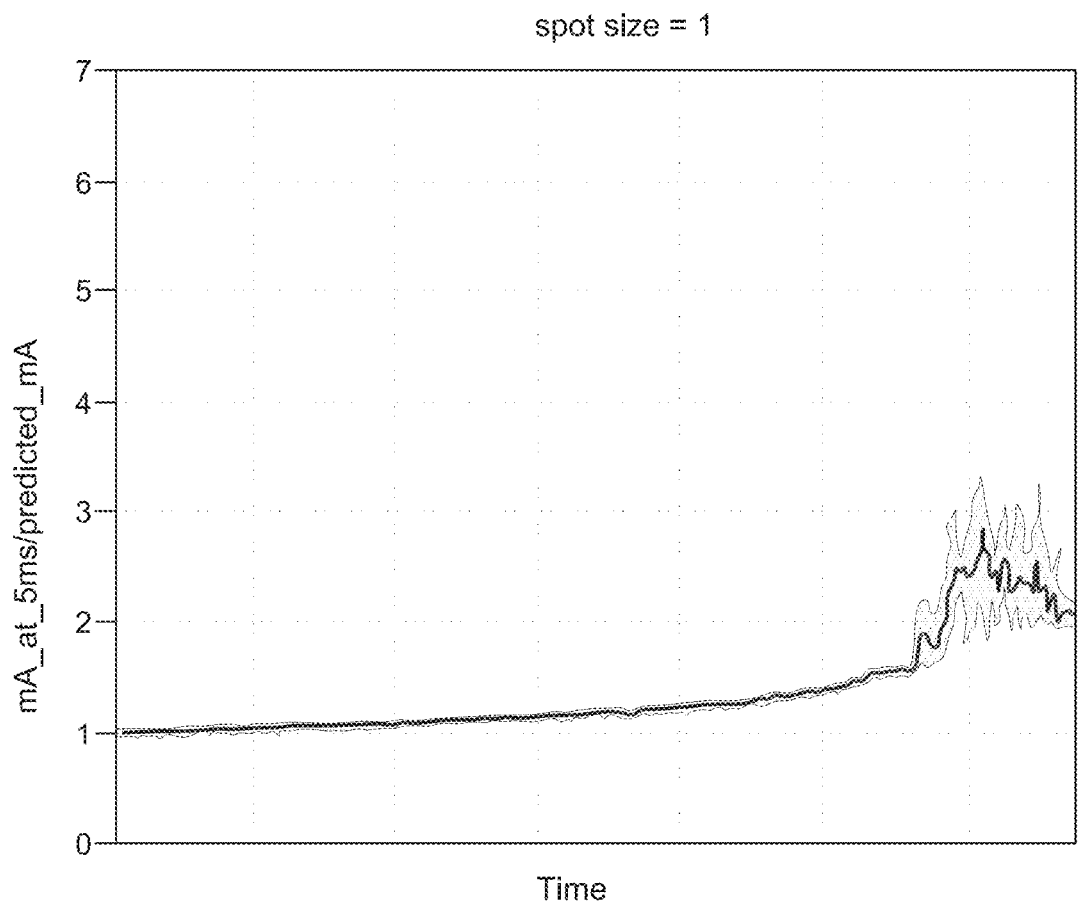
FIG. 11 depicts a trending indicator including the unstable mA behavior exhibited in FIG. 10, in accordance with aspects of the present disclosure.

In a further aspect, it may be appreciated that in addition to the remaining life and or emitter failure prediction information that may be derived in accordance with the present approach, other information may also be derived. By way of example, and turning to FIG. 10 and FIG. 11, it may be seen that information regarding an unstable mA condition may also be ascertained. For example, referring to FIG. 10, the ratio between mA at 5 ms and average mA of the X-ray tube in question becomes very unstable at a later time period. Correspondingly, turning to FIG. 11, it may be observed that the curve of the trending indicator is no longer smooth once the unstable mA condition is exhibited. Hence, it may be possible to use the present trending indicator approach to also identify other X-ray tube issues such as unstable mA, in addition to the other conditions discussed herein. Unstable mA may be caused by issues that are not related to the emitter itself, such as fluctuating pressure inside the X-ray tube, which in turn may be caused by outgassing or by vacuum leaks.

In certain embodiments, the training data set may not have enough learning points. Insufficient learning points may lead to incorrect estimation of model parameters that may cause false alarms in predicting failure of an X-ray tube filament. In such a scenario, the complexity of the model (e.g., regression model) may need to be lowered or simplified (e.g., by reducing the number of coefficients to be estimated or utilizing a model with a different form (e.g., different coefficients)). As the complexity of the model depends on the availability of different kV-mA settings in the training data, the following strategies may be utilized to count the number of operating points (e.g., kV-mA settings). These strategies include: given any kV, if there is only one mA available, the corresponding kV-mA setting will not be used for model building and indicator calculation; given any kV, for two contingent mAs (mA1<mA2), if the condition (mA2-mA1)≥20 and (mA2−mA1)/mA1≥0.2 is not satisfied, the two mAs are grouped as one mA only; count the number of unique tube voltage settings; and count the number of unique tube current settings within each tube voltage setting.

Based on the available kV-mA settings in the training data, the regression model utilized may be selected. A greater number of available kV-mA settings results in the selection of a more complex regression model having a higher number of coefficients to be estimated, while a fewer number of available kV-mA settings results in the selection of a less complex regression model having fewer coefficients to be estimated. In certain embodiments, a regression model in a different form (e.g., with different coefficients) may be utilized. Besides the number of available kV-mA settings, other criteria may be utilized in selecting the regression model. For example, a spread criteria (SC) may have to be met. Given mA spread (S) defined as, for any kV and its corresponding mAs, S=log (max (mAs))−log (min (mAs)). In order to meet the SC, the following criteria should be met. Assume $S_{max}$ is the maximum mA spread for all available kVs, there should be at least 2 kVs (if ≥3 kVs available) or 1 kV (if 2 kVs available) with their (its) mA spread greater than $0.5 \times S_{max}$; and Smax≥1.

As an example, assume the training data indicated three unique tube voltage settings, 80 kV, 100 kV, and 120 kV and for each tube voltage setting there are three tube current settings (80 kV-20 mA, 50 mA, 255 mA; 100 kV-80 mA, 200 mA, 220 mA; 120 kV-120 mA, 180 mA, 200 mA). After grouping, the tube current settings at 200 mA and 220 mA are merged for the tube voltage settings at 100 kV, and the tube current settings at 180 mA and 200 mA are also combined for the tube voltage settings at 120 kV. The tube voltage settings at 80 kV still have three tube current settings. The mA spread for the tube voltage settings at 80 kV, 100 kV, and 120 kV is 1.106, 0.398, and 0.176, respectively. As a result, the first item of the SC is not satisfied and a regression model with a reduced number of coefficients to be estimated will be selected.

The aforementioned examples assume usage of only few kV settings, which are spread out (e.g. 80 kV, 100 kV, 120 kV, 140 kV). There may also be systems that use continuous kV settings, or that use kV settings in small increments that don't inherently fulfil the SC (e.g. 80 kV, 80.1 kV, 80.2 kV, . . . ). In this case, a SC approach as described for the mA settings may also be applied to the kV settings. Alternatively, kV settings may be binned to inherently fulfil the spread criteria, e.g. by treating all kV settings close to a "nominal" kV setting as being at that nominal kV setting. An example would be to treat all kV settings with 75 kV≤x<85 kV as 80 kV when determining the regression model to be used.

Figure 12:
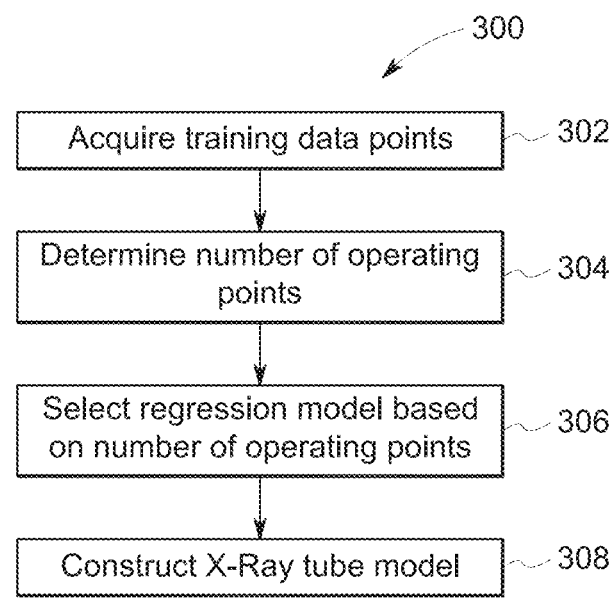
FIG. 12 depicts a flow chart illustrating a method for constructing an X-ray tube model for utilizing in assessing health of an X-ray tube, in accordance with aspects of the present disclosure.

In summary, a method 300 for constructing an X-ray tube model for utilizing in assessing health of an X-ray tube is depicted in FIG. 12. The method 300 may be performed by a processor-based system as described above. The method 300 includes acquiring training data points for a respective X-ray tube after installation of the X-ray tube in an imaging system (block 302). The method 300 also includes determining a number of operating points (e.g., kV-mA settings) utilized in the imaging system for the respective X-ray tube (block 304). The method 300 further includes selecting a regression model from a plurality of regression models based on the number of operating points (block 306), wherein each regression model uses the training data points to derive respective values for a plurality of coefficients. The method 300 even further includes constructing the X-ray tube model using the plurality of coefficients estimated by the selected regression model (block 308). Utilizing a less complex regression model (when less learning points are available) or a model in a different form (e.g., with different coefficients) may reduce or eliminate triggering false alarms in predicting X-ray tube filament failure.

Figure 13:
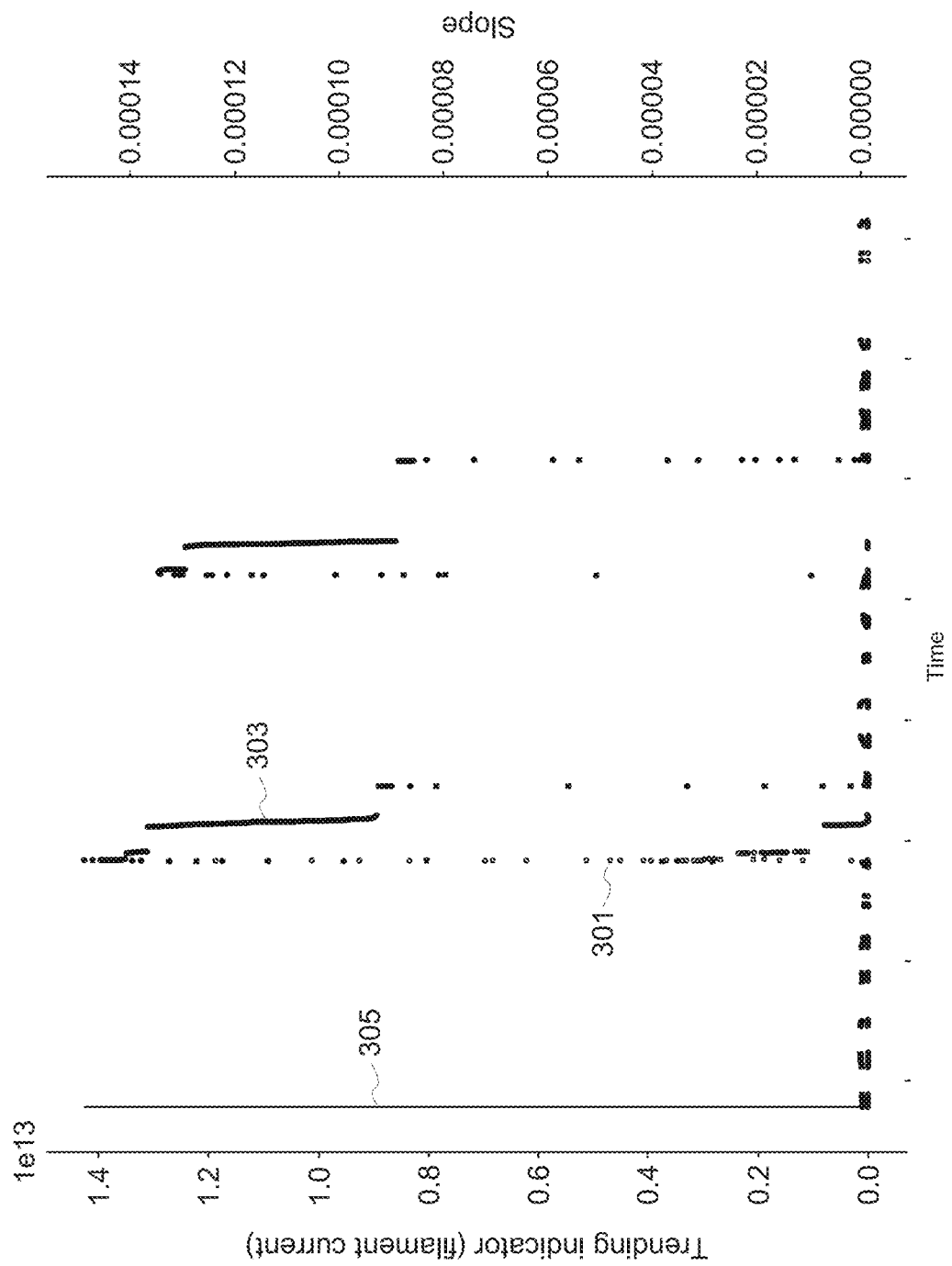
FIG. 13 depicts an example curve of a linearized combined indicator for an X-ray tube utilizing a more complex linear regression model, in accordance with aspects of the present disclosure.
Figure 14:
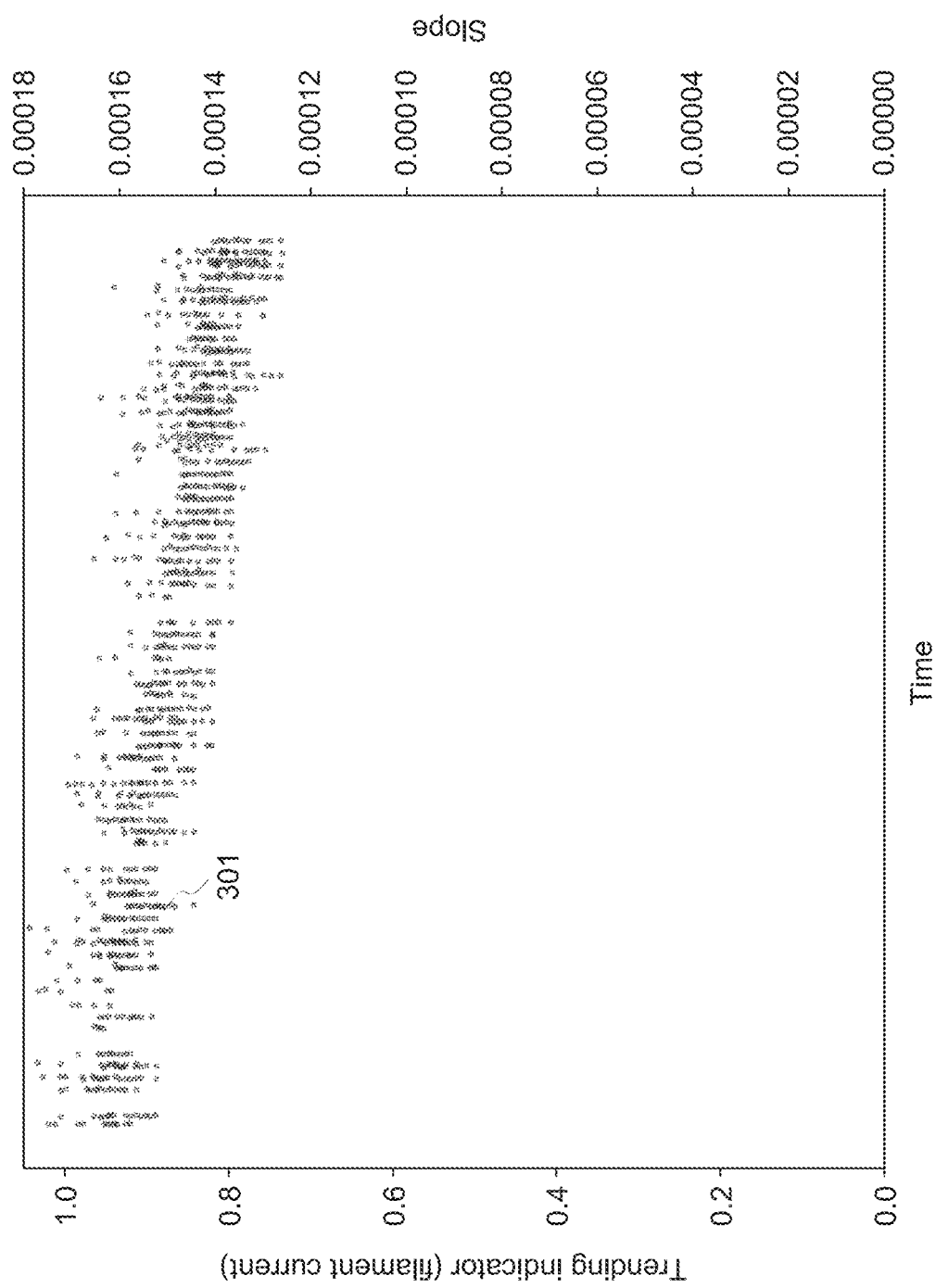
FIG. 14 depicts an example curve of a linearized combined indicator for the X-ray tube utilizing a simpler linear regression model, in accordance with aspects of the present disclosure.

FIGS. 13 and 14 provide example curves depicting a linearized combined indicator for filament current for an X-ray tube utilizing a more complex regression model and a simpler regression model, respectively. Lines 301, and 305 represent the linearized combined indicator and alarm indicator, respectively. As depicted in FIG. 13, the linearized combined indicator 301 suddenly jumps from near 0 to very large values (e.g., 10e 10 to 10e 13) before returning to normal (around 1.0) which triggers the false alarm 305. As depicted in FIG. 14, utilizing a simpler regression model resulted in no false alarms being triggered and the expected decrease in the linearized combined indicator 301 over time.

In certain situations, replacement of certain components or other service actions (e.g., filament recalibration, heater board replacement, etc.) may cause sudden changes (i.e., a jump or drop of a certain and significant percentage over a short period of time (e.g., one day or a few days)) in the calculated indicator (e.g., trend indicator) that may lead to incorrect estimation of tube life. In other situations, in some tubes, the combined indicator starts with an uptrend that can cause the combined indicator to be larger than one for quite a long time which may cause an inaccurate life estimation of tube life. The techniques below monitor for these scenarios (e.g., sudden changes in the tube life curve) and make corrections to the combined indicator.

Figure 15:
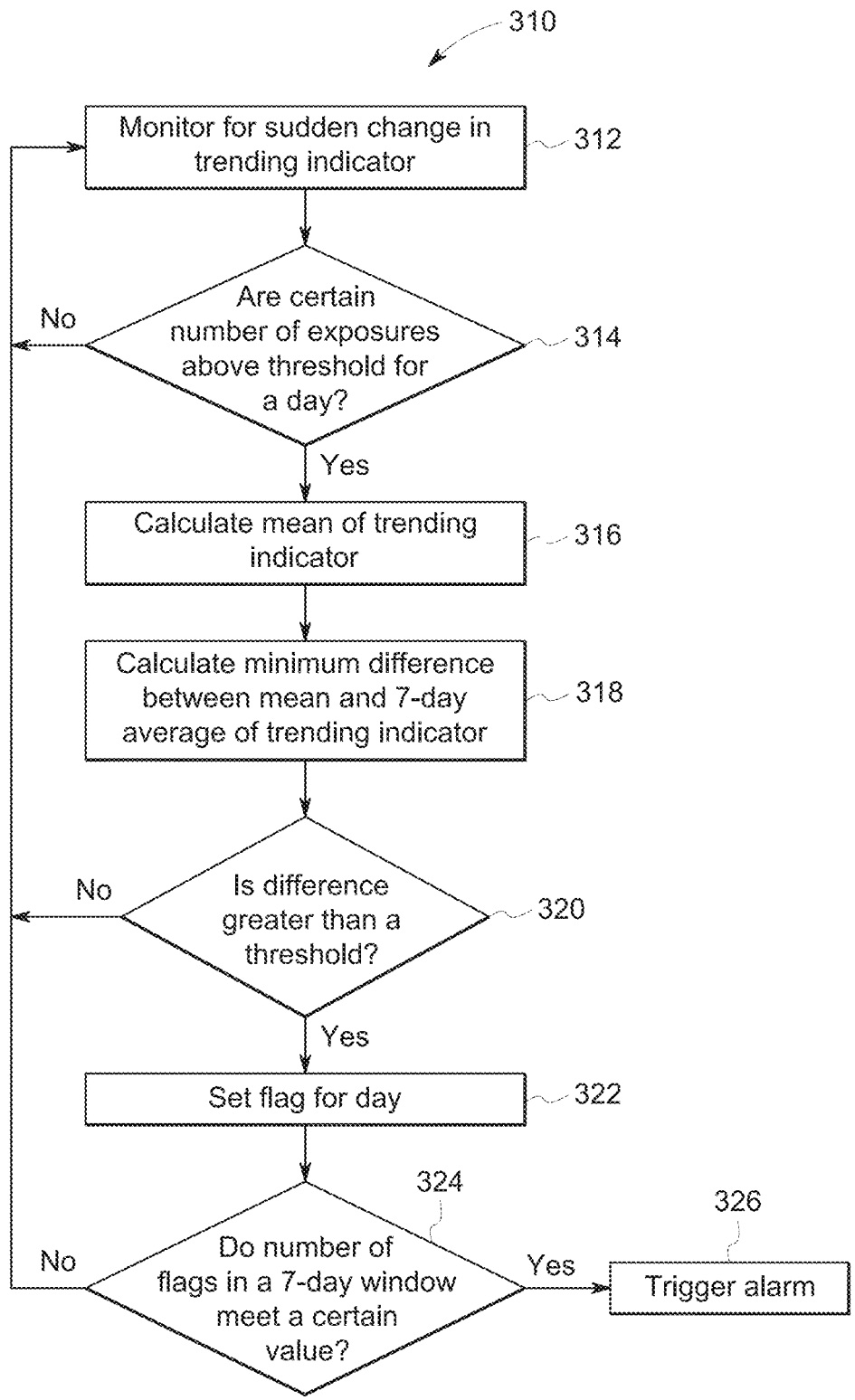
FIG. 15 depicts a flow chart illustrating a method for detecting sudden changes in a tube life curve, in accordance with aspects of the present disclosure.

FIG. 15 depicts a method 310 for detecting sudden changes in a tube life curve. The method 310 may be performed by a processor-based system as described above. The method 310 includes monitoring for a sudden change in a trending indicator (block 312). Certain rules may be implemented (e.g. utilized by the processor-based system discussed above) to detect sudden changes in a tube life curve (e.g., trending indicator). One such rule finds out on a given day, whether the mean of the trending indicator of Equation 5 shows significant changes compared with previous days. The trending indicator is utilized (rather than the linearized combined indicator) to simplify computation and reduce computing time. The method 310 includes determining whether a certain number of exposures in a given day t are above a predetermined threshold or value (block 314). The rule for change detection is as follows: at a given day t, if a given number of exposures (e.g., 10 or another predetermined number) is above a threshold, calculate a mean of the trending indicator of Equation 5 as $\overline{Irel(t)}$ (block 316), otherwise, no action is taken (i.e., monitoring for a sudden change continues (block 312)); calculate a minimum of the difference between $\overline{Irel(t)}$ and the previous 7-day average trending indicator as $\mathrm{Dif}_{min}$= MIN $(\overline{Irel(t)}-\overline{Irel(t-1)}, \ldots, \overline{Irel(t)}-\overline{Irel(t-7)})$ (block 318); determine if $\mathrm{Dif}_{min}$ is greater than a threshold (block 320), where if $\mathrm{Dif}_{min} > \mu$, where $\mu$ is a threshold set at a predetermined value (e.g., 0.006, which represents around 6-7 percent tube life), set a flag for day t as flag$_t$=1 (block 322); and determine if the number of days in a set window meet a certain value (block 324). For example, for a consecutive 7-day window (or other window with a different number of days), if 4 (or another number days) of them have the flag set at 1, trigger an alarm (e.g., providing a notification of an alarm) (block 326) to indicate a change is detected. Of note, the day when the change happens will be the one that has the first flag set at 1 within the 7-day window, rather than the day on which the alarm is triggered. If the number of days does not meet the value, then continue monitoring for a sudden change (block 312).

Figure 16:
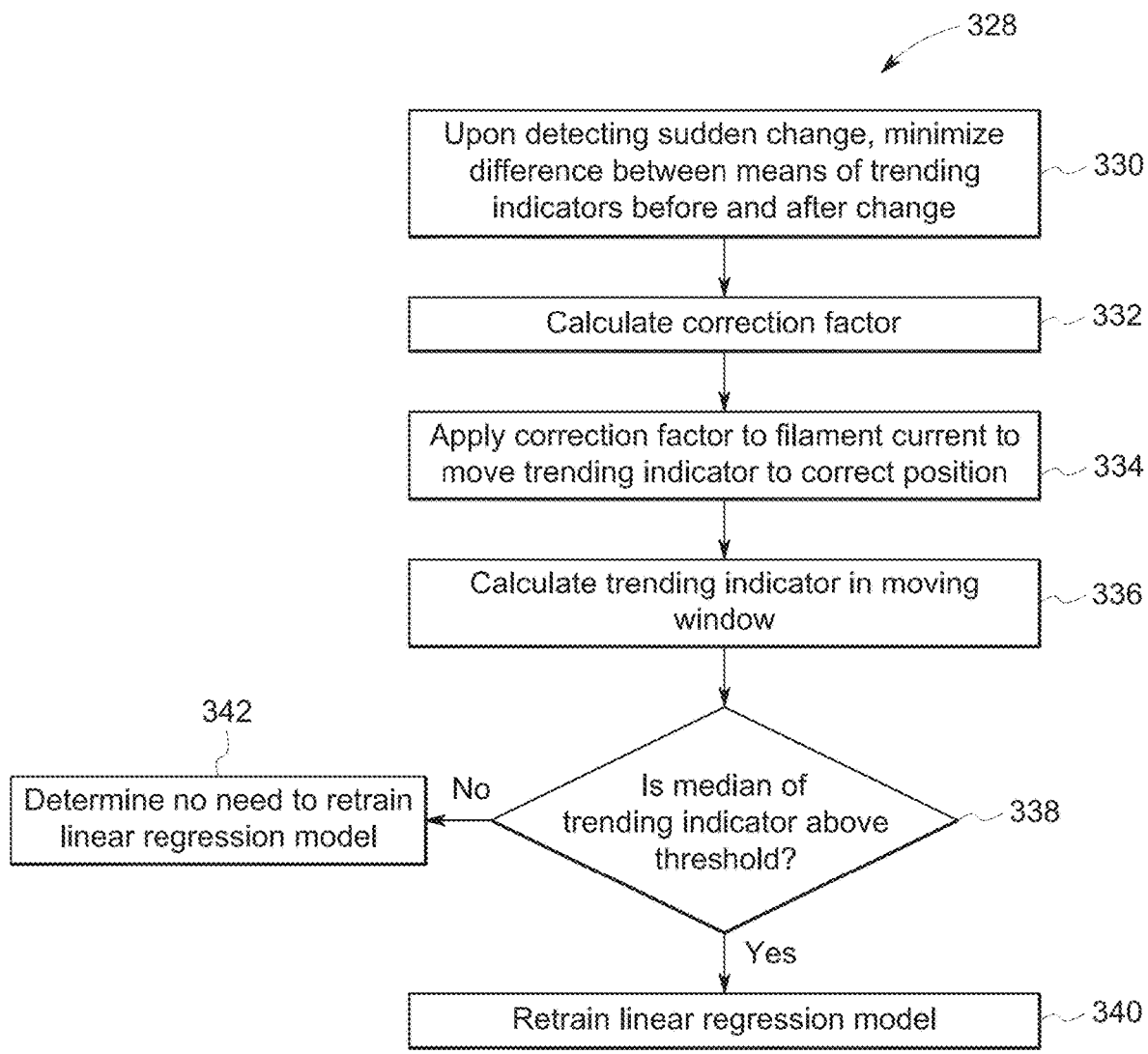
FIG. 16 depicts a flow chart illustrating a method for correcting a sudden change in a tube life curve and retraining a linear regression model, in accordance with aspects of the present disclosure.

Once a change is detected, corrections need to be made to the filament current (Filament_Current_in_Preheat) to move the trending indicator curve back to the right position. FIG. 16 depicts a flow chart illustrating a method 328 for correcting a sudden change in a tube life curve and retraining a linear regression model. The method 328 may be performed by a processor-based system as described above. For example, suppose a sudden jump or drop is detected on day t, the objective function of the correction procedure is to minimize the difference between the means of trending indicators before and after the change (block 330), $$\text{Minimize} |\overline{Irel(t+1)} - \overline{Irel(t-1)}|. \tag{13}$$

By using Equation 5, the mean of the trending indicator on day t+1 can be written as, $$\overline{Irel(t+1)} = \frac{1}{N_{t+1}} \sum_{i=1}^{N_{t+1}} \left( \frac{(\alpha I_{fil}^i)^{2/3}}{(I_{fil}^{i\,est})^{2/3}} - 1 \right), \tag{14}$$

where $\alpha$ is the correction factor applied to the filament current after the change happens and $N_{t+1}$ is the number of exposures on day t+1.

By setting Equation 13 to 0, we have, $$\left| \frac{1}{N_{t+1}} \sum_{i=1}^{N_{t+1}} \left( \frac{(\alpha I_{fil}^i)^{2/3}}{(I_{fil}^{i\,est})^{2/3}} - 1 \right) - \overline{Irel(t-1)} \right| = 0, \tag{15}$$

which leads to, $$\left| \alpha^{2/3} \frac{1}{N_{t+1}} \sum_{i=1}^{N_{t+1}} \left( \frac{(I_{fil}^i)^{2/3}}{(I_{fil}^{est})^{2/3}} \right) - 1 - \overline{Irel(t-1)} \right| = 0. \tag{16}$$

Therefore, the correction factor $\alpha$ can be calculated (block 332) as, $$\alpha = \left( (1 + \overline{Irel(t-1)}) \Big/ \frac{1}{N_{t+1}} \sum_{i=1}^{N_{t+1}} \left( \frac{(I_{fil}^i)^{2/3}}{(I_{fil}^{est})^{2/3}} \right) \right)^{3/2}. \tag{17}$$

Upon calculating the correction factor, the method 328 includes applying the correction factor to the filament current to move the trending indicator to the correct position (block 334).

Figure 17:
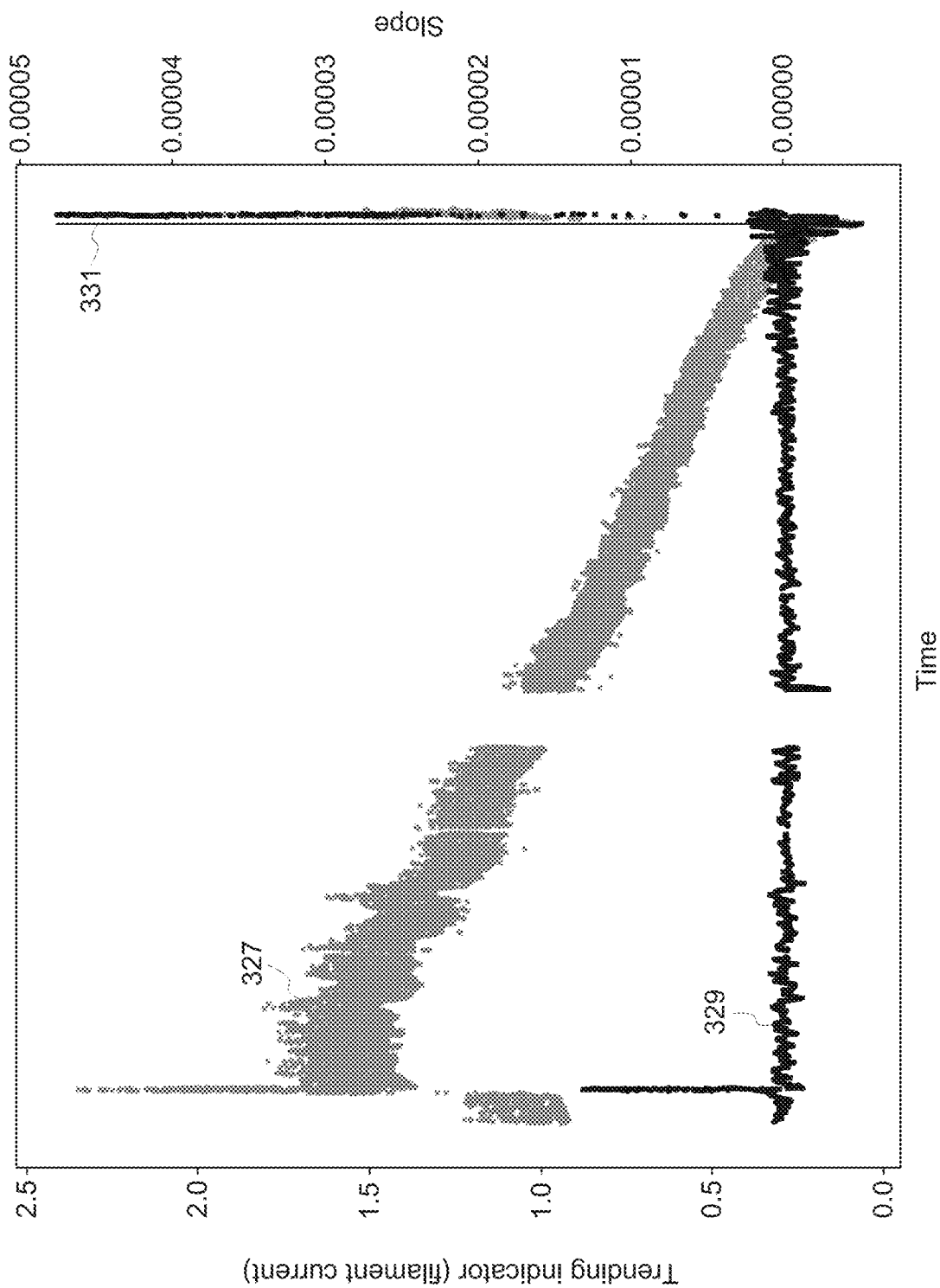
FIG. 17 depicts an example curve of a linearized combined indicator for an X-ray tube (without correction), in accordance with aspects of the present disclosure.
Figure 18:
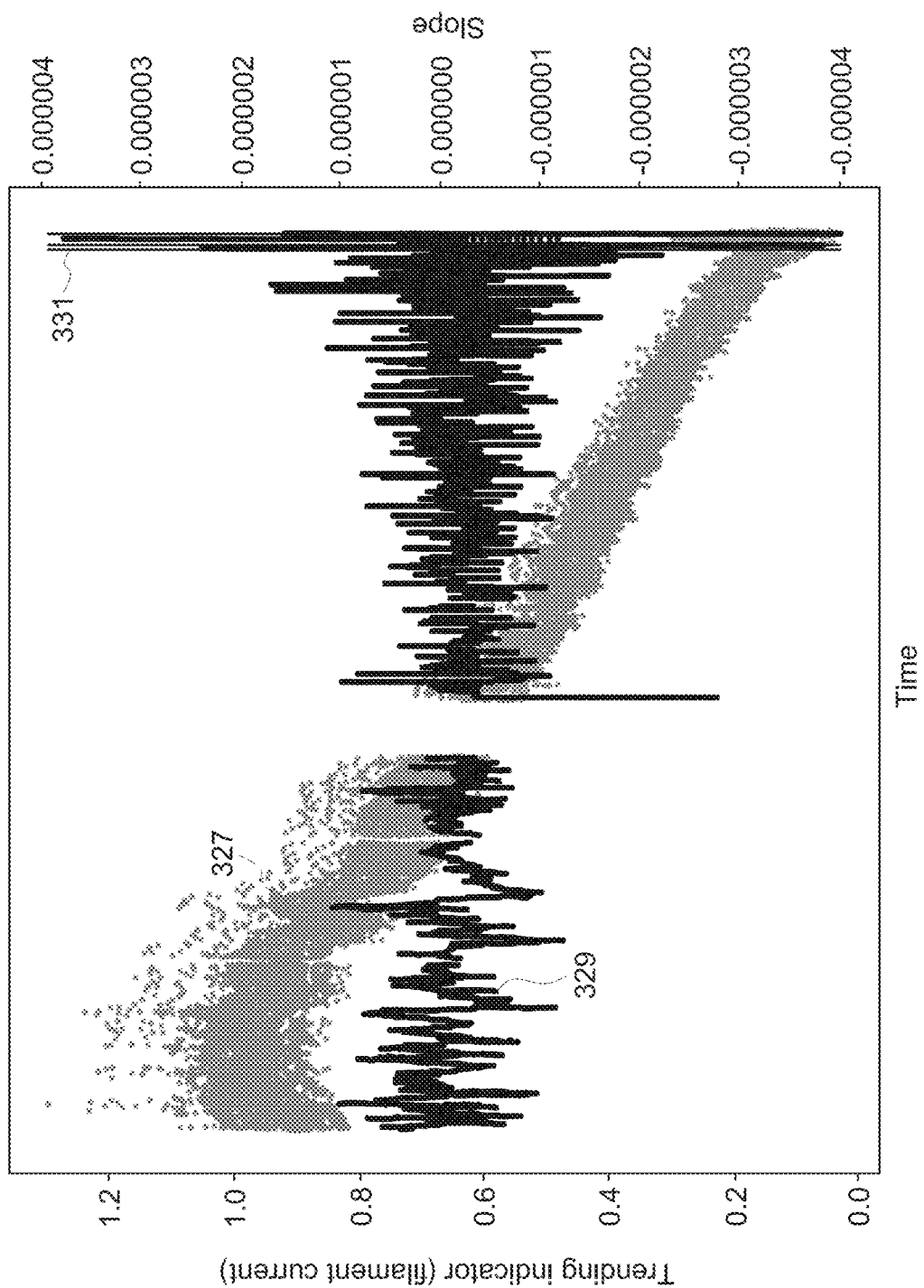
FIG. 18 depicts an example curve of a linearized combined indicator for an X-ray tube (with correction), in accordance with aspects of the present disclosure.

FIGS. 17 and 18 provide example curves depicting a linearized combined indicator for filament current and corresponding slope over time for an X-ray tube without and with correction, respectively. Lines 327, 329, and 331 represent the linearized combined indicator, slope, and alarm indicator, respectively. As depicted in FIG. 17, the linearized combined indicator 303 suddenly jumps from approximately 1 to approximately 1.5 early on. As depicted in FIG. 18, the sudden jump is detected and corrected by utilizing the techniques described above.

To address the issue that the tube life may have more than 100 percent life left, a continuous learning mechanism may be applied to dynamically update the trained linear regression model that describes the relations between tube voltage, tube current, and filament current. Similar to the change detection rule discussed above, it is determined whether retraining is needed based on the calculated trending indicator. From Equation 5, ideally, the trending indicator will start from 0 and gradually decrease as the filament becomes thinner. However, in some cases, the values of the trending indicator may be much larger than 0. Thus, the trained linear model no longer captures the evaporative thinning of the filament, and the model needs to be recalibrated.

Returning to FIG. 16, to retrain the model, we maintain a moving window W with size set at 1,000. The method 328 includes calculating the trending indicator in the moving window (block 336). The method 328 further includes determining if the median of the trending indicator is above a predetermined threshold (block 338). If the median of the trending indicator in the moving window is above the threshold (e.g., set at 0.001 or another value), the linear regression model will be retrained by using the data points from the moving window (block 340), with outliers removed based on the following rules. Given trending indicator $I^{rel}(t)$ in the moving window, the outliers are identified as points with (mA_at_5 ms(t)/(Average_mA(t))>1.2, or (mA_at_5 ms(t))/(Average_mA(t))<0.8, or $I^{rel}(t) \geq \text{Mean}(W)+3.0 \times \text{Std}(W)$, or $I^{rel}(t) \leq \text{Mean}(W)-3.0 \times \text{Std}(W)$. If the median of the trending indicator in the moving window is not above the threshold, the method 328 includes determining to not retrain the linear regression model (block 342).

It should be noted that a decision regarding retraining occurs after the change detection step. In other words, if a sudden change is detected, the filament current will be corrected first and then the trending indicator calculated (which is used to determine whether model retraining is needed).

Figure 19:
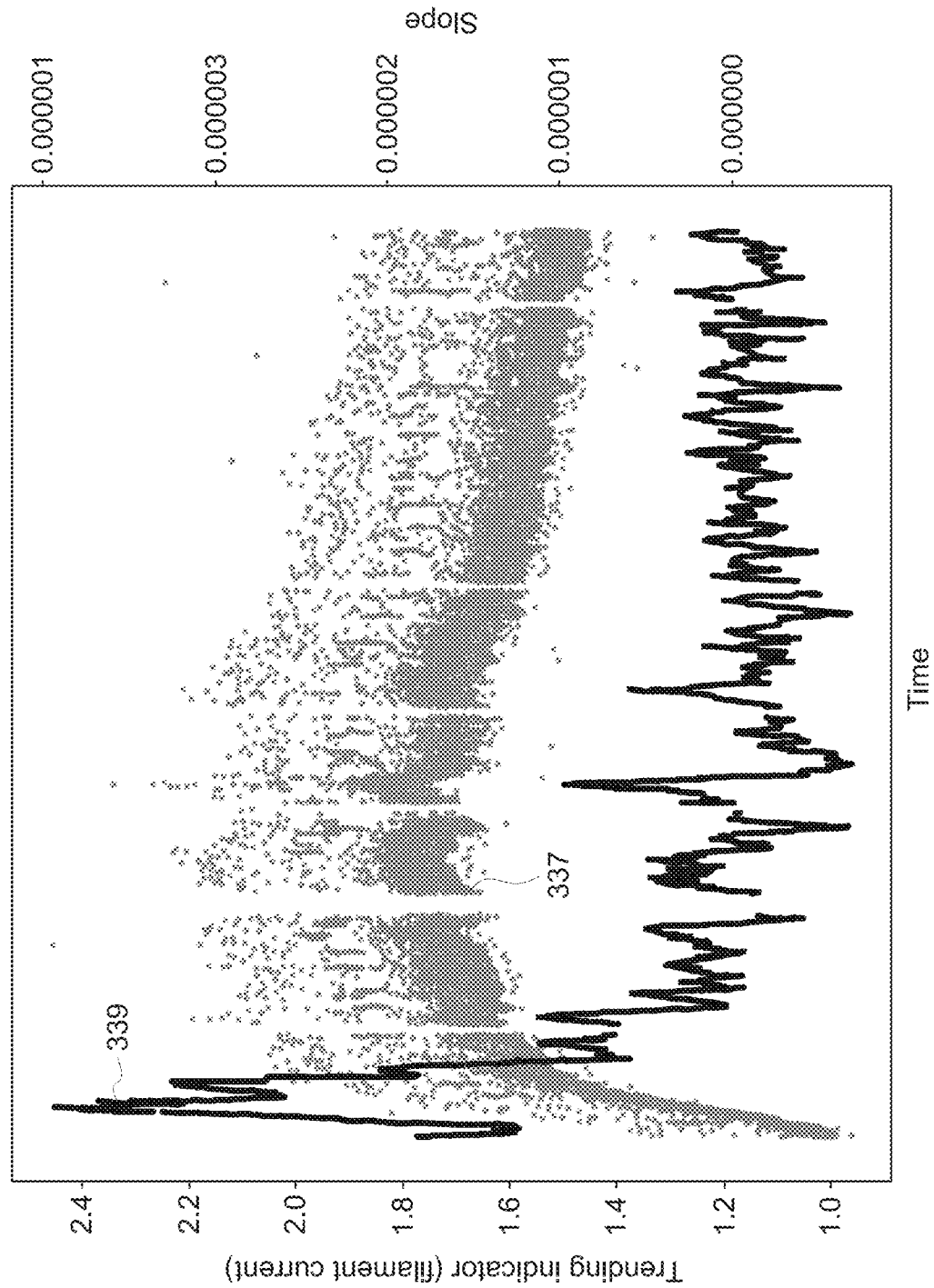
FIG. 19 depicts an example curve of a linearized combined indicator for an X-ray tube (without retraining), in accordance with aspects of the present disclosure.
Figure 20:
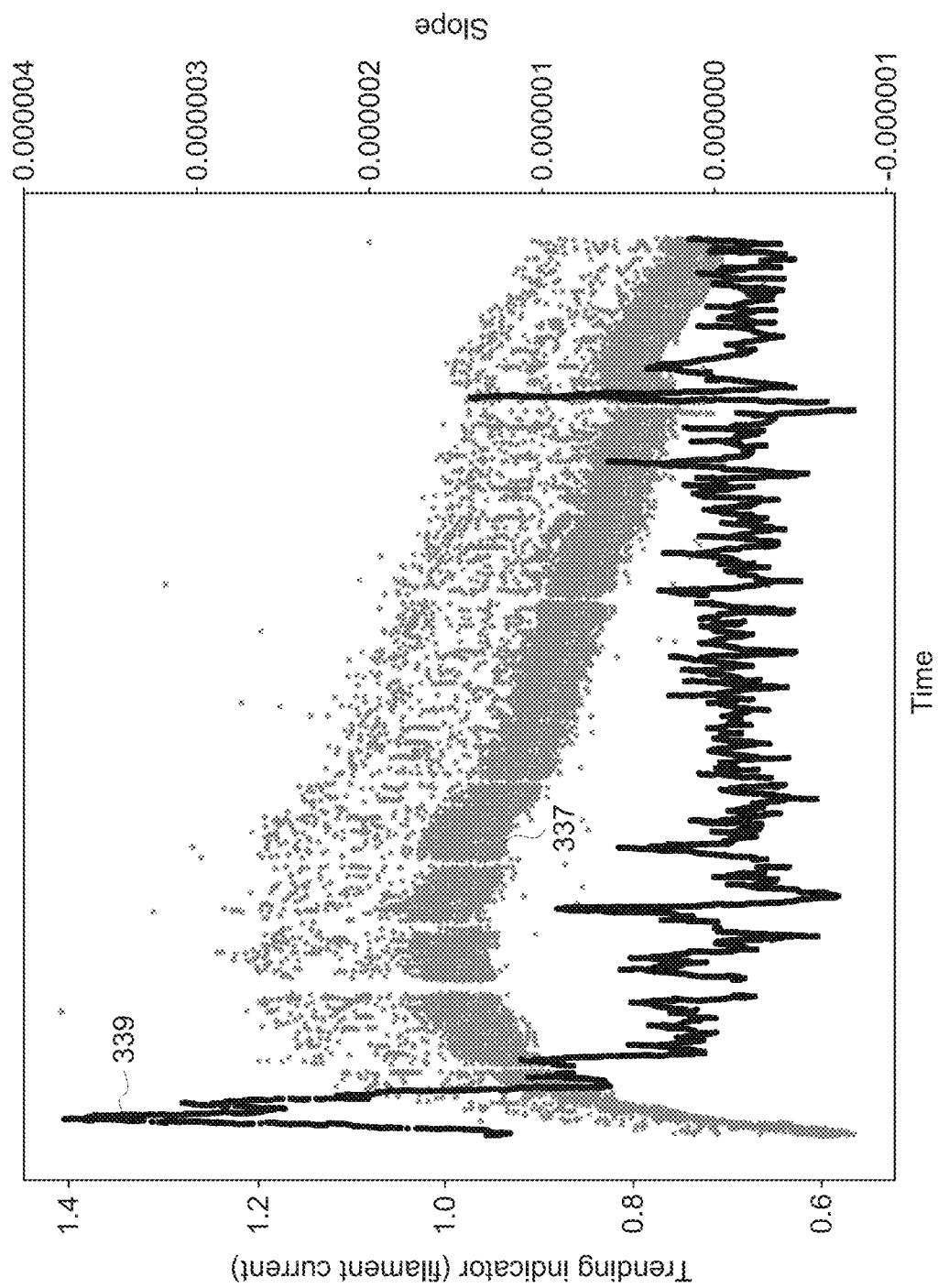
FIG. 20 depicts an example curve of a linearized combined indicator for an X-ray tube (with retraining), in accordance with aspects of the present disclosure.
Figure 21:
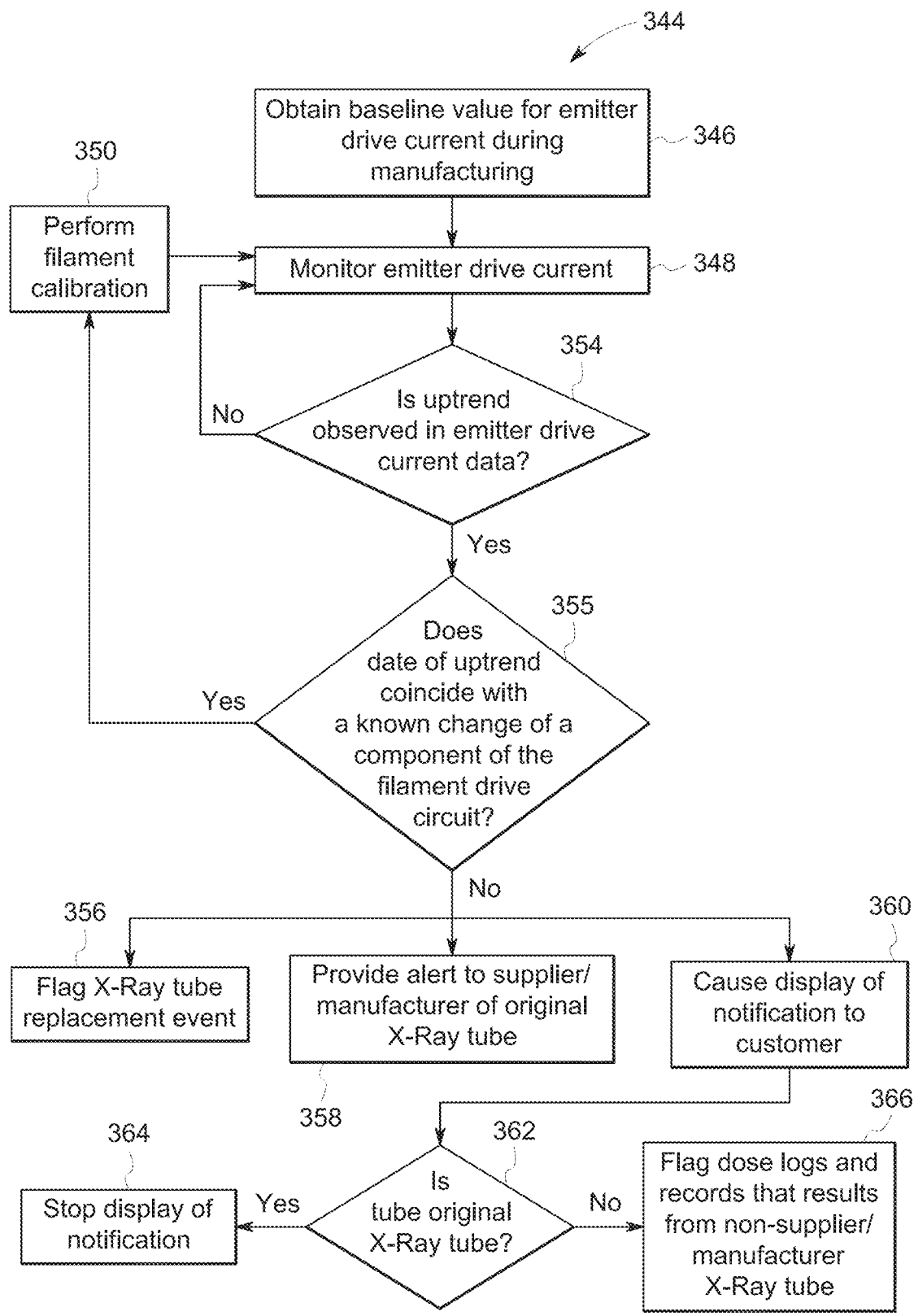
FIG. 21 depicts a flow chart illustrating a method for monitoring for X-ray tube replacement, in accordance with aspects of the present disclosure.

FIGS. 19 and 20 provide example curves depicting a linearized combined indicator for filament current and corresponding slope over time for an X-ray tube without and with retraining, respectively. Lines 337 and 339 represent the linearized combined indicator and slope, respectively. As depicted in FIG. 19, at the beginning of tube life, the linearized combined indicator 337 jumps from approximately 1 to approximately 1.8 early on. As depicted in FIG. 20, after application of retraining, the linearized combined indicator 337 peaks at around 1.0 early on, as opposed to 1.8.

The X-ray tube is the most frequently replaced part in an imaging system. It is expected that an approved/authorized X-ray tube (i.e., from the manufacturer/supplier) gets replaced with another approved/authorized X-ray tube when the original X-ray tube is used up. However, due to third party availability, a non-genuine X-ray tube (i.e., not approved or authorized by the manufacturer/supplier) may be utilized to replace the original X-ray tube. The non-genuine X-ray tube can be easily configured as a genuine one (i.e., approved/authorized X-ray tube) without informing the manufacturer/supplier of the original X-ray tube and system. This activity causes all dose and other critical parameters related to exposure getting logged/assigned to the original approved/authorized X-ray tube despite the actual X-ray tube being a third party replacement. The manufacturer/supplier of the original X-ray tube has an interest in knowing the status of any X-ray tube change activity and keeping a log of authorized X-ray tube replacements. These activities can be regularly checked against authorized service requests. Any discrepancy can help the manufacturer/supplier of the original X-ray tube to identify systems running on a third party X-ray tube and to take the proper course of actions to ensure these third party tubes are not configured as X-ray tubes of the original manufacturer/supplier.

In certain embodiments, the techniques described above for predicting X-ray tube failure may be utilized to monitor filament current values to automatically detect X-ray tube replacement. When a new X-ray tube is installed in the field as a replacement part or is installed into a system for the first time, its power unit (i.e., generator), performs filament calibration using filament current. This value obtained during calibration is utilized to keep track of the filament aging process. As described above, as the filament ages, the current required to heat the prescribed filament to the prescribed temperature reduces in value as the filament itself reduces in size due to evaporation.

The trending algorithm discussed above enables tracking of the filament current values (which typically is a decreasing trend over time). It should be noted that depending on the variable related to emitter resistance tracked, the trend may increase over time. In certain embodiments, tracking of these filament current values is performed discretely and is run as a core process that ensures complete non-visibility and secrecy. As described below, when the existing X-ray tube is used up and replaced by a new X-ray tube (or a component of the filament drive circuit coupled to the X-ray tube (e.g., outside the X-ray tube)), the trending algorithm (discussed above) and historical record will detect the anomaly (i.e., replacement of X-ray tube or component of the filament drive circuit). The (suspected) X-ray tube change event (or component of the filament drive circuit change event) may trigger an alert that is displayed on the system. For systems monitored by the manufacturer/supplier of the system, the (suspected) X-ray tube change event may send an alert to the manufacturer/supplier. The manufacturer/supplier can verify the event by looking at the system identification number and associated service requests associated with that system (e.g., to see if an X-ray tube replacement was scheduled). In certain embodiments, for a non-connected system (i.e., not connected to the manufacturer/supplier via the internet), detection of the (suspected) X-ray tube event may result in a notification(s) (e.g., pop-up alert(s)) to be displayed or provided to the customer informing the customer to contact the manufacturer/supplier of the X-ray tube or component of the filament drive circuit. If the X-ray tube replacement or replacement for the component of the filament drive circuit is done by the genuine manufacturer/supplier of the original X-ray tube or component (via manufacturer/supplier-approved field engineers), the notifications or pop-up alerts can be switched off (e.g., using proprietary replacement X-ray tubes of the manufacturer/supplier). The pop-up alerts may be recurrent, until the manufacturer/supplier is contacted to look into the matter. Upon a visit of a field engineer from the manufacturer/supplier to the site, the necessary action can be taken (i.e., determining if the original X-ray tube was replaced with a third party X-ray tube and switching off the alerts).

FIG. 18 depicts a flow chart illustrating a method 344 for monitoring for X-ray tube replacement or replacement of a filament drive circuit coupled to the X-ray tube (e.g., outside the X-ray tube). The method 344 may be performed by a processor-based system described above. The method 344 includes obtaining a baseline value for emitter drive current of an X-ray tube (e.g., original approved or authorized X-ray tube) during manufacturing (block 346). This value may be stored within a memory and accessed by the processor-based system. Obtaining this baseline value occurs during system staging in manufacturing, where the system logs filament aging current during the manufacturing staging. Once the system is installed at the customer site and commissioned, the method 344 includes monitoring a variable related to emitter resistance (e.g., emitter drive current (e.g., filament aging current)) (block 348). Monitoring of the variable related to emitter resistance (e.g., emitter drive current) occurs as described above with the data being stored and trended. Over time the emitter drive current is expected to trend downward. As noted above, another variable related to emitter resistance may trend upward.

The method 344 includes determining if a sudden change in one direction (e.g., an uptrend (e.g., significant uptrend)) is observed in the emitter drive current data or other variable related to emitter resistance (block 354). In some embodiments, the sudden change (e.g., uptrend) must reach a certain threshold (e.g., 20 percent or another value depending on X-ray tube filament design). If a sudden change (e.g., an uptrend (e.g., significant uptrend)) is not observed, the method 344 includes continuing to monitor the emitter drive current or other variable related to emitter resistance (block 348). If a sudden change is observed, the method 344 includes determining if a date of the sudden change (e.g., uptrend) coincides with a known change of a component of the filament drive circuit or an X-ray tube (block 355). If the sudden change does coincide with a known change, the method 344 includes performing filament calibration (block 350). The system logs the calibration value with or without knowing if the X-ray tube or component is replaced. After filament calibration, the method 344 further includes continuing to monitor the emitter drive current or other variable related to emitter resistance (block 348). If the sudden change does not coincide with a known change, the method 344 includes flagging a (potential) X-ray tube replacement event or replacement event for a component of a filament drive circuit (block 356). In certain embodiments (e.g., when the system is connected to the manufacturer/supplier via the internet), if a sudden change is observed, the method 344 includes providing an alert to the supplier/manufacturer of the original X-ray tube or component (block 358). In certain embodiments (e.g., when the system is not in communication with the manufacture/supplier), if a sudden change is observed, the method 344 includes providing or causing display of a notification (e.g., pop-up alert) to the customer of the potential event (block 360). The next action(s) are based on a determination if the X-ray tube or component is from the original manufacturer/supplier (block 362). If a customer does not contact the original manufacturer/supplier, the notifications or pop-up alerts may continue. If the customer does contact the original manufacturer/supplier, a field engineer may visit the site to investigate the X-ray tube. If the X-ray tube or component is a tube or component of the manufacturer/supplier, the notifications or pop-up alerts may be stopped or switched off (block 364) via a received tube certificate or input from a service menu. If the X-ray tube or component is from a third party, the system flags the dose logs and records that results are from a third party X-ray tube or component (block 366). In certain embodiments, acknowledgment from the customer of replacing the original X-ray tube or component with a third party tube may avoid a visit from a field engineer and the system flags the dose logs and records that results are from a third party X-ray tube or component (block 366).

Detecting X-ray tube replacement events enables the original supplier/manufacturer to keep track of customers that have switched to third party X-ray tubes and to target those customers about the advantages of an authorized or approved X-ray tube from the supplier/manufacturer. Increasing the number of authorized X-ray tubes may lead to lower production cost due to increased volumes. In addition, existing contracts between the original supplier/manufacturer may be renegotiated with customers that switch to third party X-ray tubes. Tube quality affects the function of the components connected to the tube and, thus, the warranty of the generator, power module, and high voltage cables may need to be renegotiated. Further, early failures of other high voltage components may be at least partially chargeable even if a site is under an extended maintenance contract but has used up the X-ray tube entitlement by utilizing a third party X-ray tube. Similarly, addressing image quality issues and dose logging may be chargeable even if a site is under an extended maintenance contract but has used up the X-ray tube entitlement by utilizing a third party X-ray tube. Even further, costs of service related to the X-ray tube may be passed on to the customer due to the presence of a lower-quality X-ray tube. Further, a supplier/manufacturer can track the quality of third party X-ray tubes.

Technical effects of the disclosed subject matter include generating one or both of a failure prediction indication for an X-ray tube or a remaining useful life estimate for the X-ray tube. In one implementation, a trained static tube model is used in estimating health (e.g., thickness) of the electron emitter of the X-ray tube, which in turn may be used in predicting failure of the tube and/or estimating remaining useful life of the tube. In another implementation, replacement of an X-ray tube may be detected.

This written description uses examples to disclose the subject matter, including the best mode, and also to enable any person skilled in the art to practice the disclosed subject matter, including making and using any devices or systems and performing any incorporated methods. The patentable scope of the disclosed subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for constructing an X-ray tube model for utilizing in assessing health of an X-ray tube, comprising:
    acquiring training data points for a respective X-ray tube after installation of the X-ray tube in an imaging system;
    determining a number of operating points utilized in the imaging system for the respective X-ray tube; and
    selecting a regression model from a plurality of regression models based on the number of operating points, wherein each regression model uses the training data points to derive respective values for a plurality of coefficients.

2. The method of claim 1, wherein the operating points comprise mA-kV settings that characterize each respective training data point.

3. The method of claim 1, wherein each regression model of the plurality of regression models comprises a different number of coefficients for the plurality of coefficients, or a different form of the regression model.

4. The method of claim 1, comprising constructing the X-ray tube model using the plurality of coefficients estimated by the selected regression model.

5. The method of claim 4, wherein the X-ray tube model returns an estimate of a variable related to emitter resistance in response to input data points.

6. The method of claim 4, wherein the X-ray tube model comprises a model relating X-ray tube voltage and electron emitter current with X-ray tube current.

* * * * *